(12) United States Patent
Otsubo et al.

(10) Patent No.: US 10,702,199 B2
(45) Date of Patent: Jul. 7, 2020

(54) BLOOD COLLECTING DEVICE

(71) Applicant: Hitachi High-Technologies Corporation, Tokyo (JP)

(72) Inventors: Ayano Otsubo, Tokyo (JP); Yoshihiro Nagaoka, Tokyo (JP); Taku Sakazume, Tokyo (JP); Kenko Uchida, Tokyo (JP); Shigenori Togashi, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 297 days.

(21) Appl. No.: 15/579,957

(22) PCT Filed: Apr. 27, 2016

(86) PCT No.: PCT/JP2016/063125
§ 371 (c)(1),
(2) Date: Dec. 6, 2017

(87) PCT Pub. No.: WO2016/203853
PCT Pub. Date: Dec. 22, 2016

(65) Prior Publication Data
US 2018/0220944 A1    Aug. 9, 2018

(30) Foreign Application Priority Data

Jun. 17, 2015 (JP) .................. 2015-121633

(51) Int. Cl.
*A61B 5/15* (2006.01)
*A61B 5/022* (2006.01)
(Continued)

(52) U.S. Cl.
CPC .......... *A61B 5/150099* (2013.01); *A61B 5/02* (2013.01); *A61B 5/022* (2013.01);
(Continued)

(58) Field of Classification Search
CPC ..... A61B 5/150099; A61B 5/02; A61B 5/151; A61B 5/022; A61B 5/15; A61B 5/150351;
(Continued)

(56) References Cited

U.S. PATENT DOCUMENTS 2,442,111 A * 5/1948 Beardsley ........... A61F 13/0203
602/58
4,298,011 A * 11/1981 Mangurten ........ A61B 5/15003
435/304.2
(Continued)

FOREIGN PATENT DOCUMENTS

| CN | 201341885 Y | 11/2009 |
| JP | 07-213925 A | 8/1995 |

(Continued)

OTHER PUBLICATIONS

International Search Report of PCT/JP2016/063125 dated Aug. 23, 2016.
(Continued)

*Primary Examiner* — Eric F Winakur
*Assistant Examiner* — Abid A Mustansir
(74) *Attorney, Agent, or Firm* — Mattingly & Malur, PC

(57) ABSTRACT

A blood collecting device collects blood in a short time after puncture without scattering the blood into the open air other than a container for collecting the blood. One of representative blood collecting devices has a container unit that includes a screw portion, a holder that holds the container unit serving as a system whose one end is closed, a puncture unit that can be attached to the container or the holder, a through-hole of the puncture unit, and a puncture unit protection member that protects the puncture unit and the container unit.

10 Claims, 25 Drawing Sheets

(51) Int. Cl.
  *A61B 5/151* (2006.01)
  *A61B 5/02* (2006.01)
  *A61B 5/154* (2006.01)

(52) U.S. Cl.
  CPC ............ *A61B 5/15* (2013.01); *A61B 5/151* (2013.01); *A61B 5/150343* (2013.01); *A61B 5/150351* (2013.01); *A61B 5/150748* (2013.01); *A61B 5/154* (2013.01); *A61B 5/150435* (2013.01)

(58) Field of Classification Search
  CPC ............ A61B 5/150343; A61B 5/154; A61B 5/150435
  See application file for complete search history.

(56) References Cited

U.S. PATENT DOCUMENTS

| | | | | |
|---|---|---|---|---|
| 4,687,479 | A * | 8/1987 | Sarstedt | B01L 3/50825 422/916 |
| 5,569,287 | A | 10/1996 | Tezuka et al. | |
| 6,315,738 | B1 * | 11/2001 | Nishikawa | A61B 5/150022 600/583 |
| 2004/0186500 | A1 * | 9/2004 | Koike | A61B 5/150022 606/181 |
| 2005/0283083 | A1 * | 12/2005 | Lee | A61B 5/02225 600/490 |
| 2007/0083131 | A1 | 4/2007 | Escutia et al. | |
| 2008/0077048 | A1 * | 3/2008 | Escutia | A61B 5/1411 600/583 |
| 2010/0261988 | A1 | 10/2010 | Tamir | |
| 2010/0323437 | A1 * | 12/2010 | Nakae | B01L 3/50825 435/307.1 |
| 2014/0296744 | A1 * | 10/2014 | Wei Li | A61B 5/15003 600/577 |

FOREIGN PATENT DOCUMENTS

| | | |
|---|---|---|
| JP | 9-266889 A | 10/1997 |
| JP | 2002-219115 A | 8/2002 |
| JP | 2006-068384 A | 3/2006 |
| JP | 2008-054884 A | 3/2008 |
| JP | 2009-509679 A | 3/2009 |
| WO | 2006/025608 A1 | 3/2006 |
| WO | 2008/027319 A1 | 3/2008 |

OTHER PUBLICATIONS

Chinese Office Action received in corresponding Chinese Application No. 201680033834 dated Nov. 21, 2019.
Japanese Office Action received in corresponding Japanese Application No. 2015-121633 dated Feb. 19, 2019.

* cited by examiner

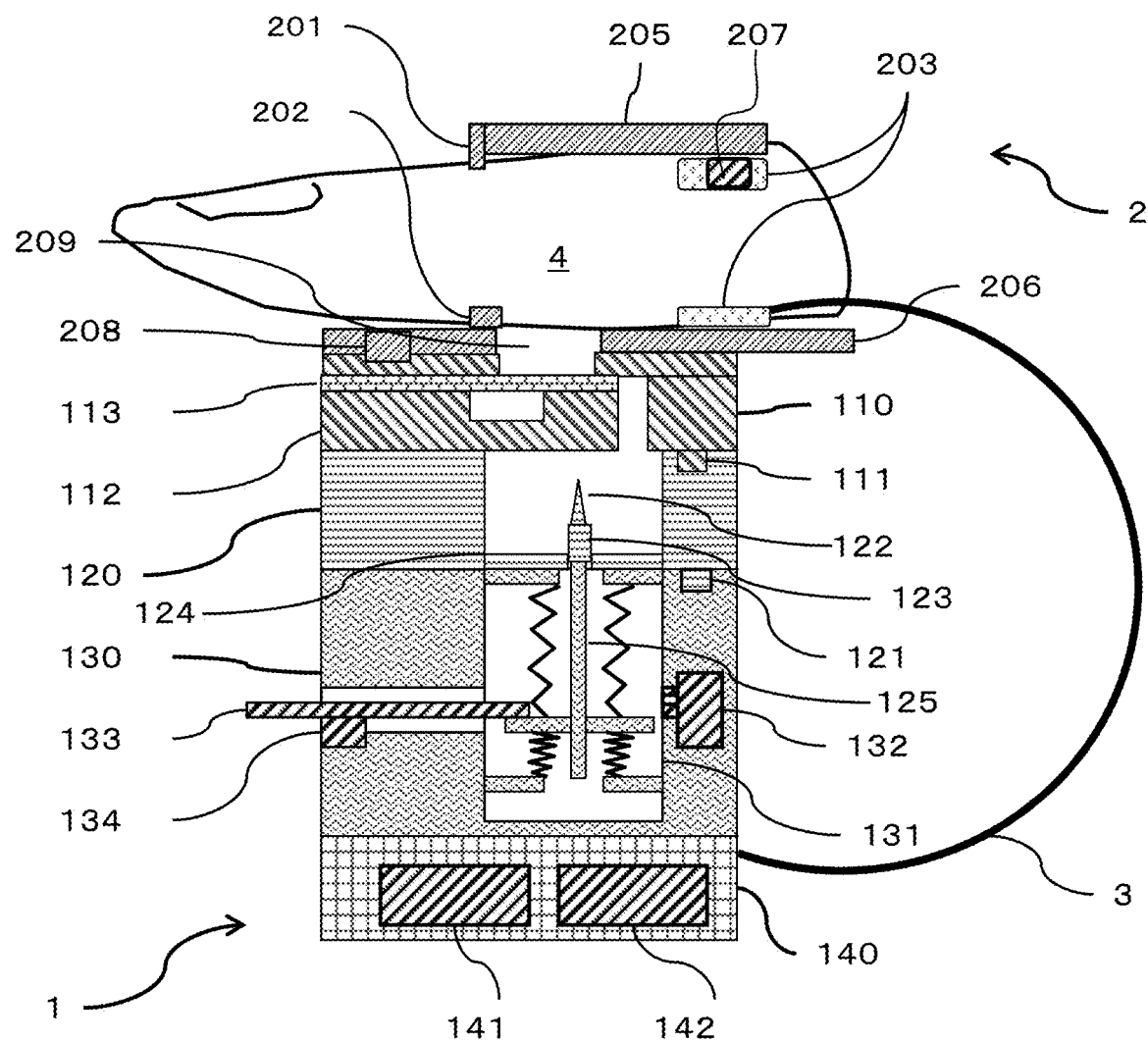

[Fig. 1B]
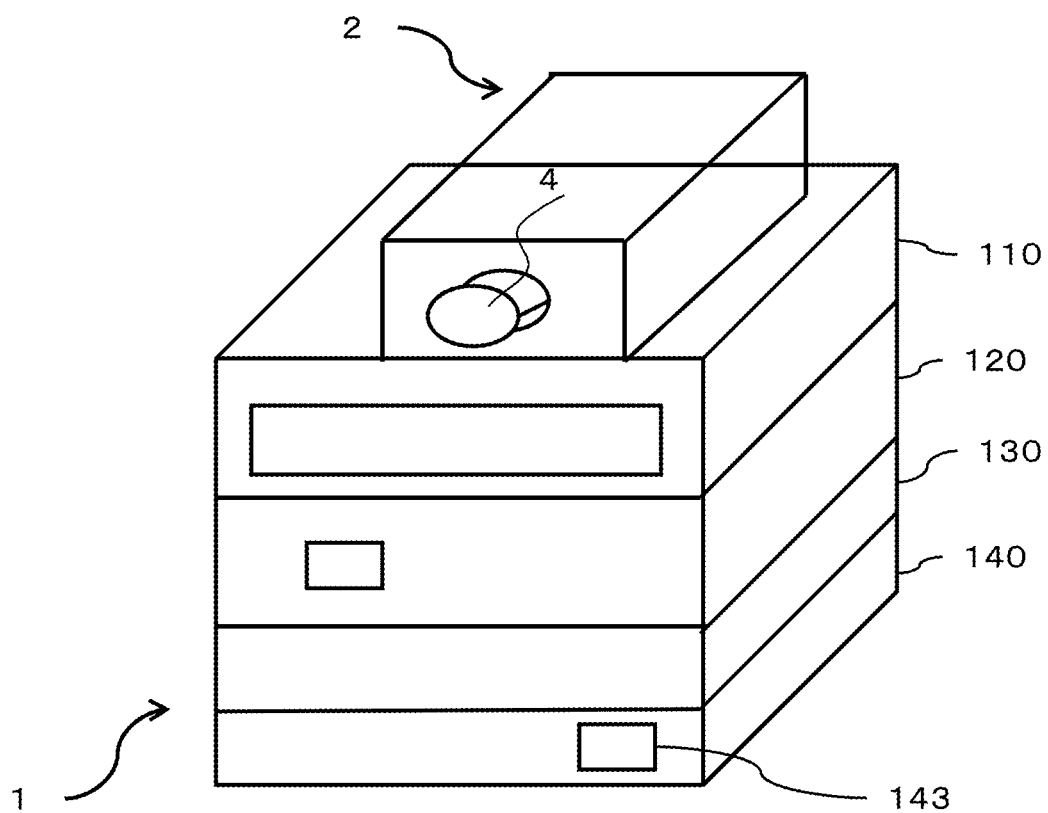

[Fig. 1C]
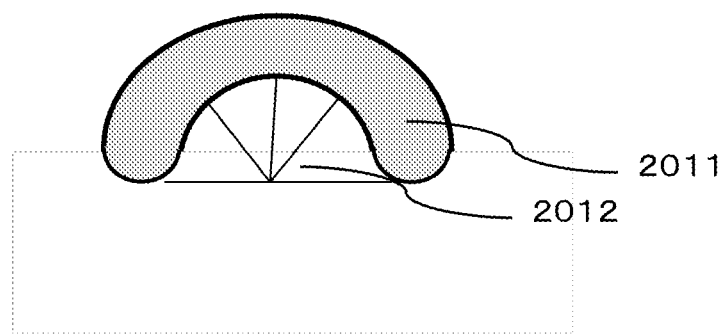
[Fig. 1D]
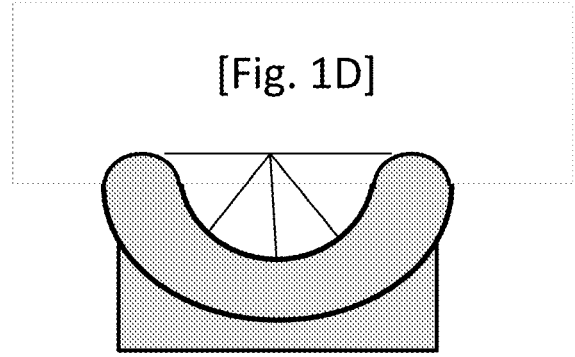
[Fig. 1E]
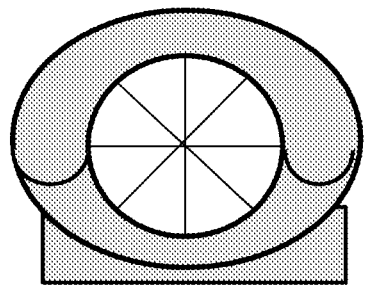

[Fig. 2]
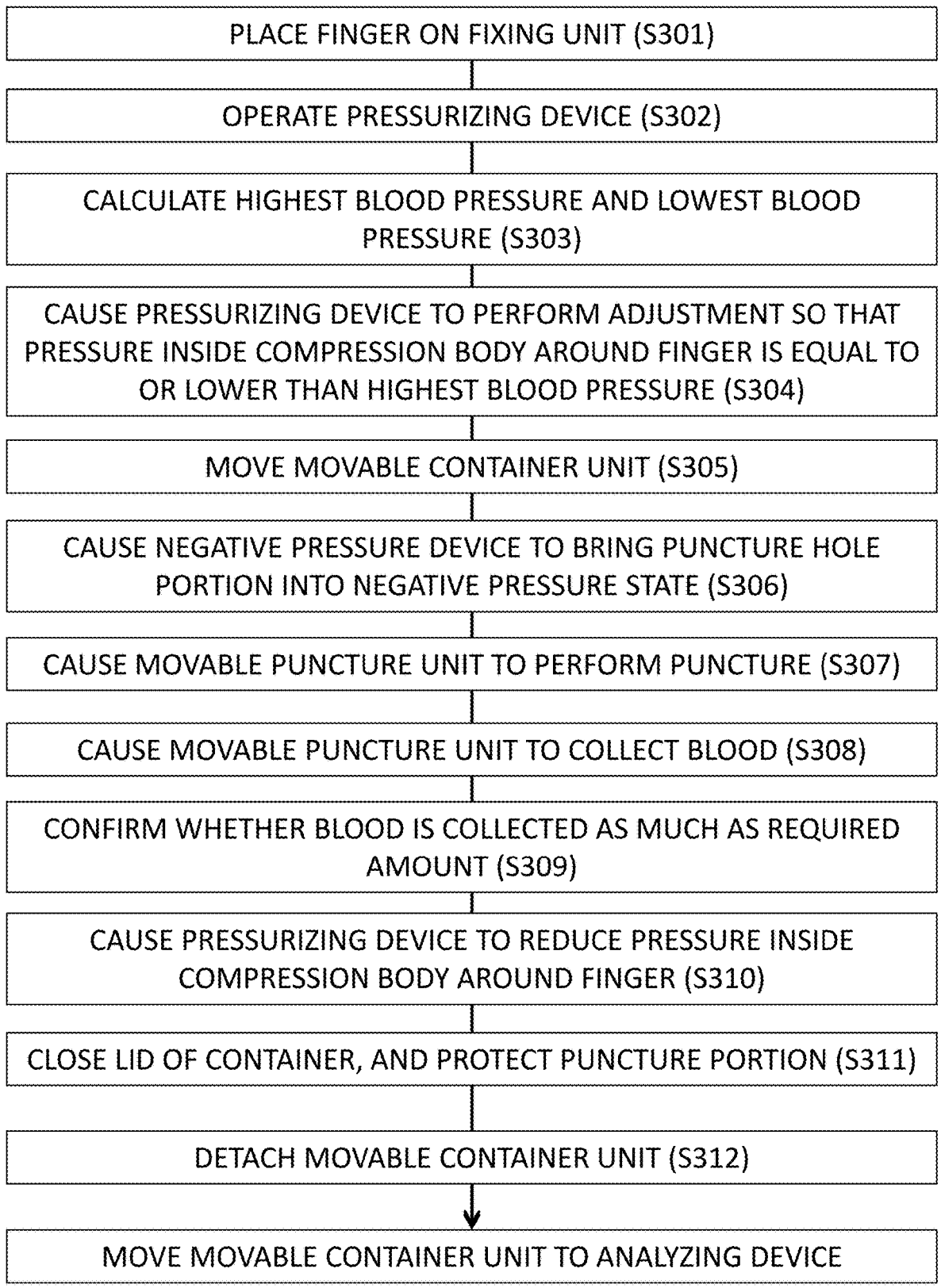

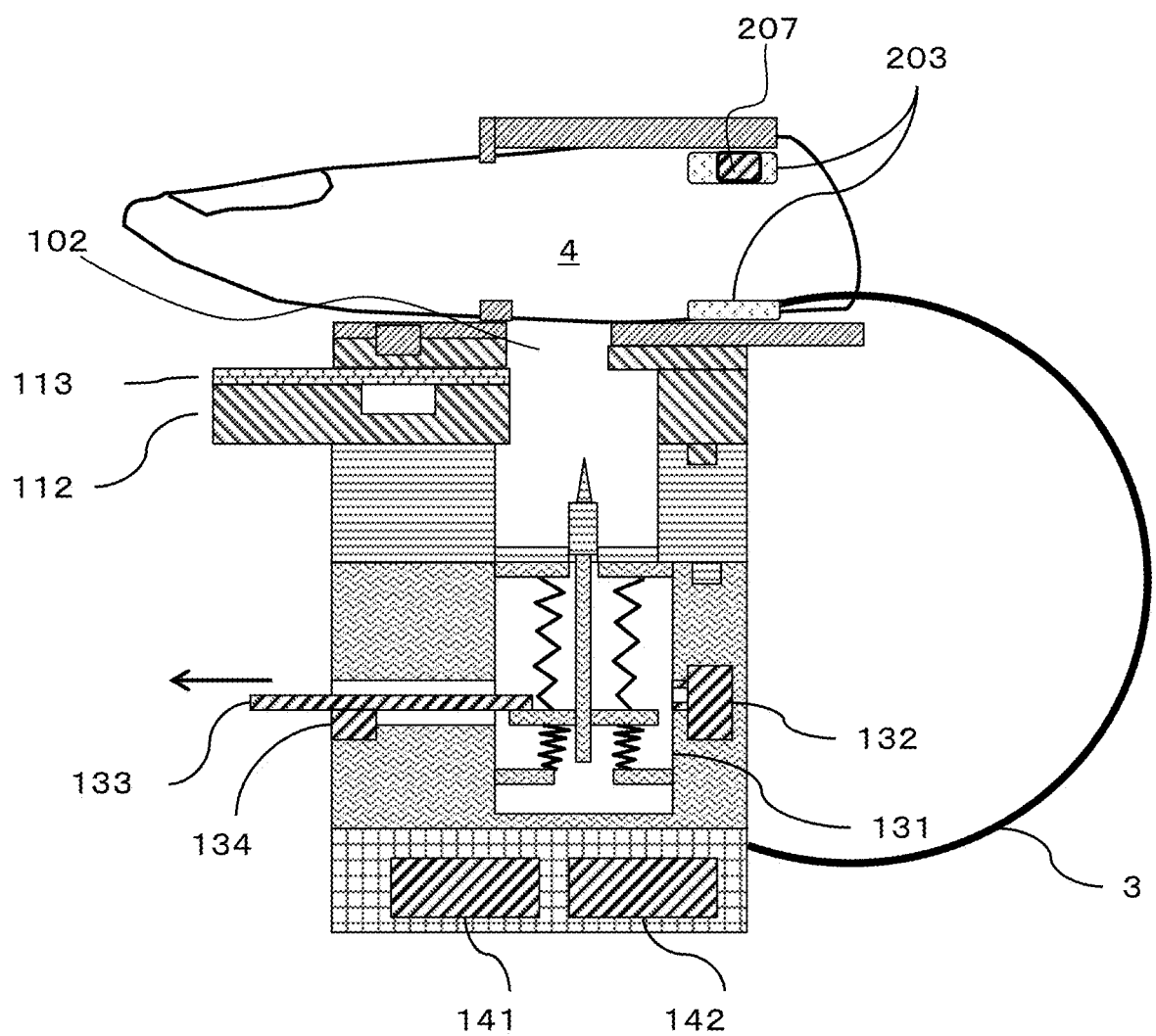
[Fig. 3A]

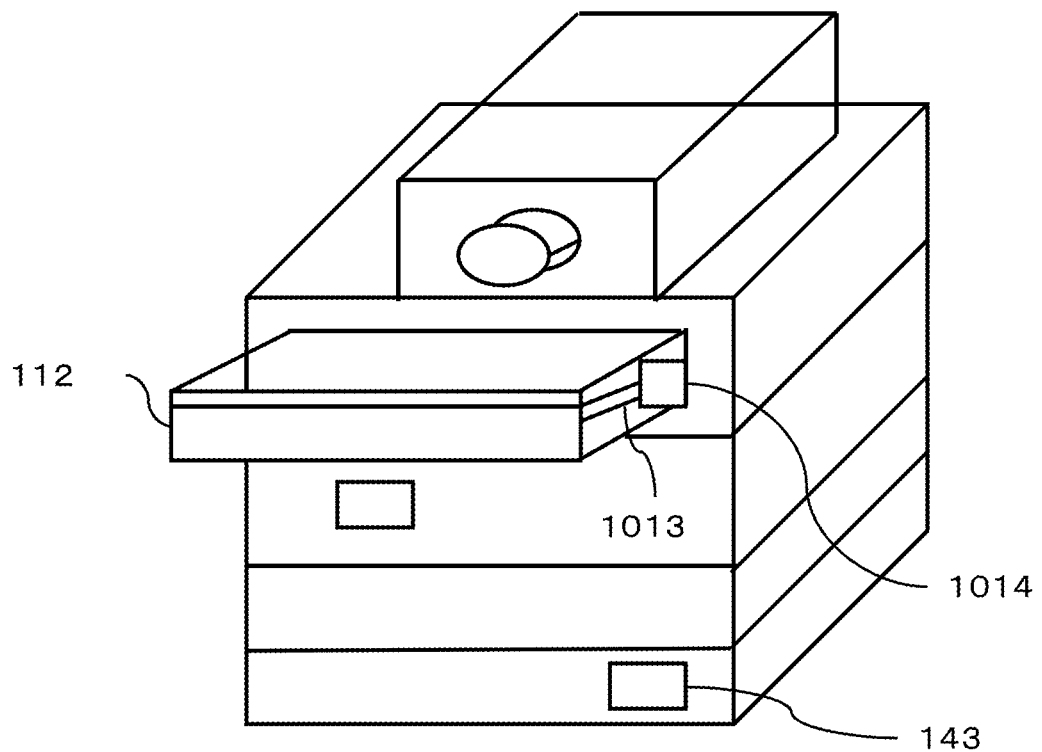
[Fig. 3B]

[Fig. 4A]
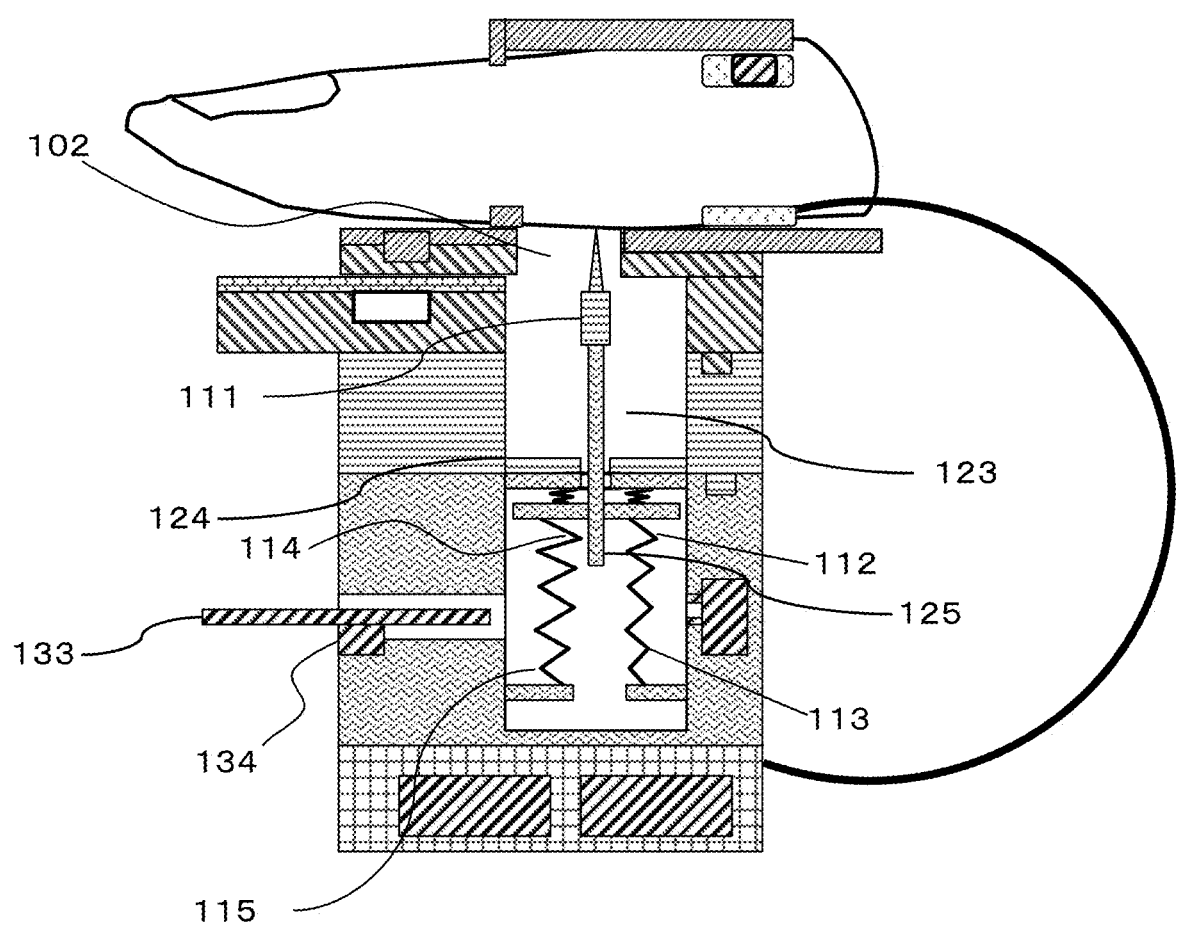

[Fig. 4B]
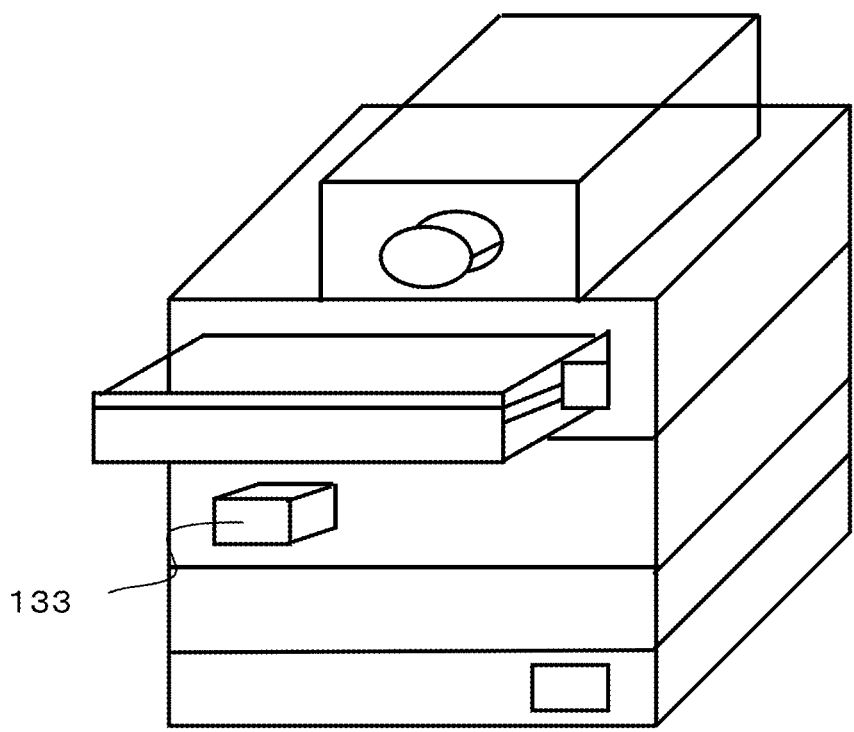
133

[Fig. 5]
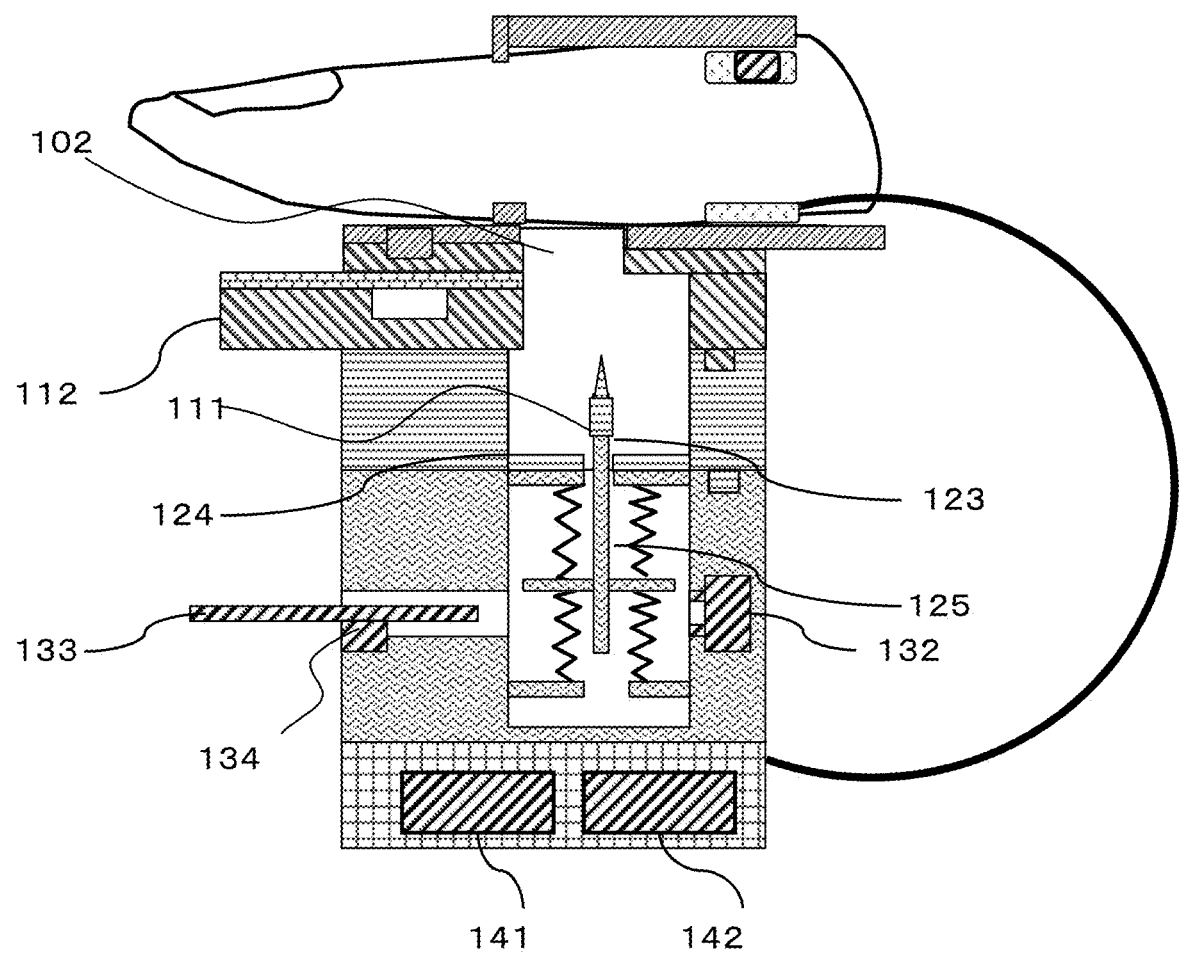

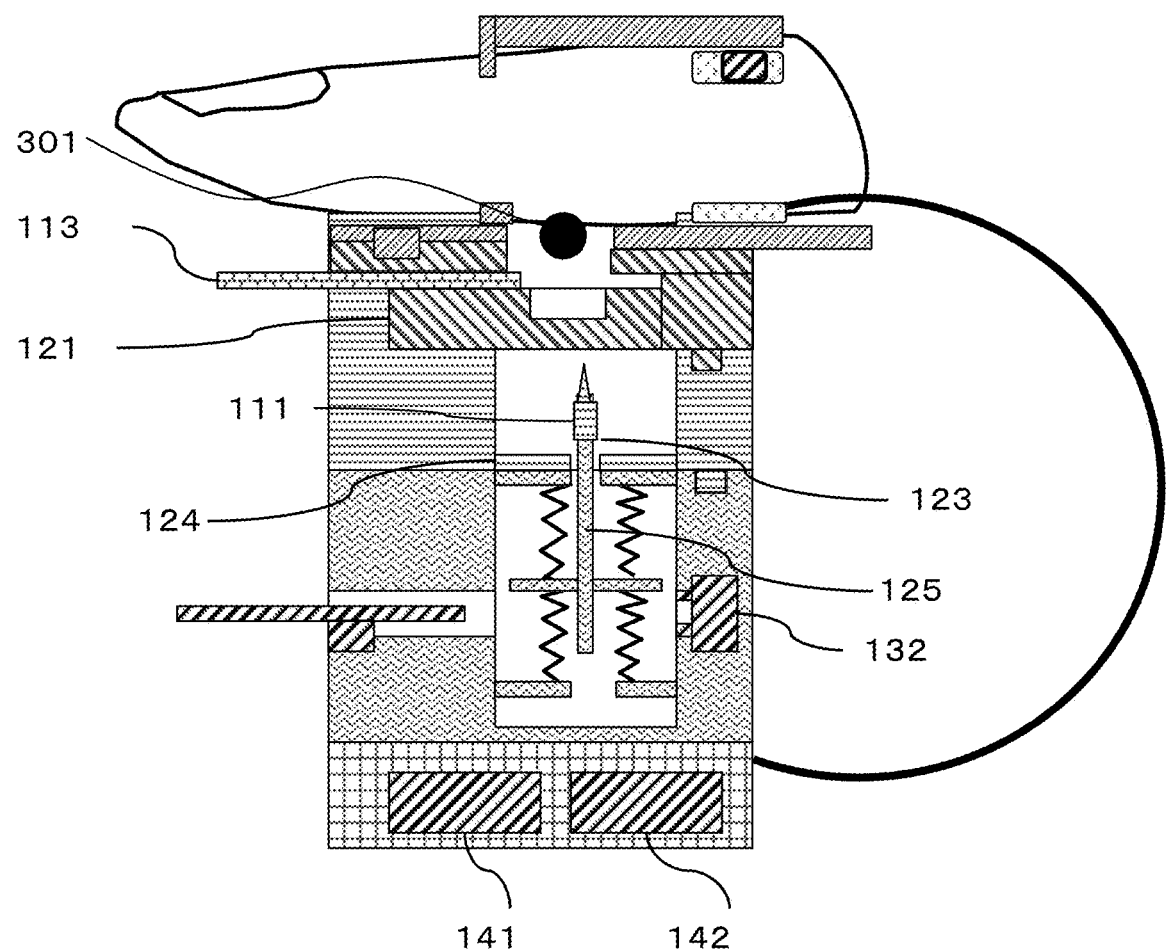
[Fig. 6A]

[Fig. 6B]
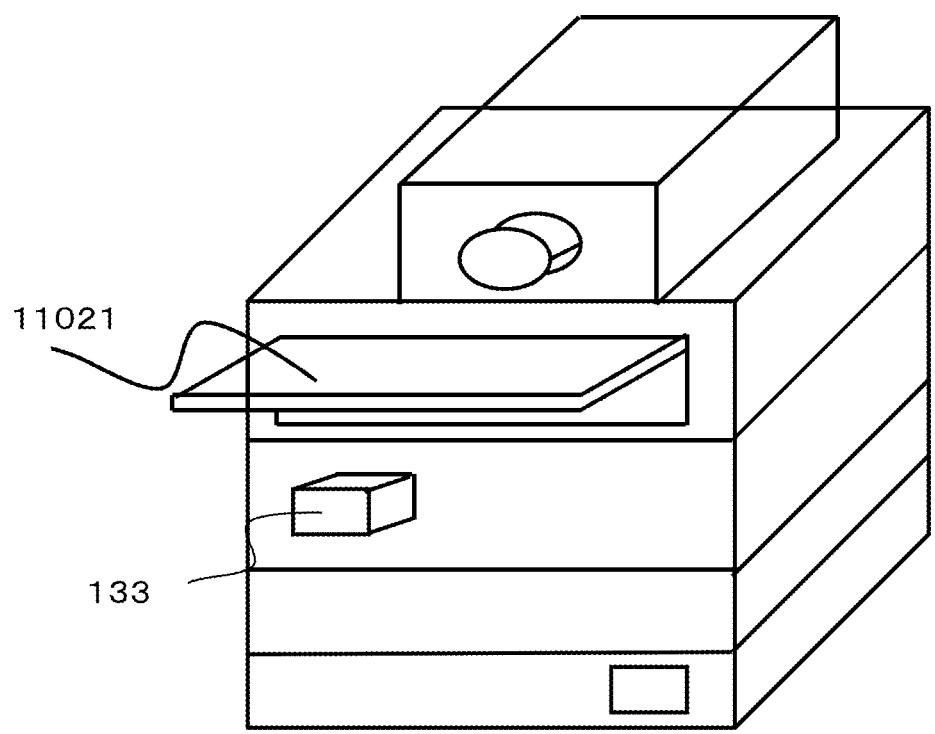

[Fig. 7A]
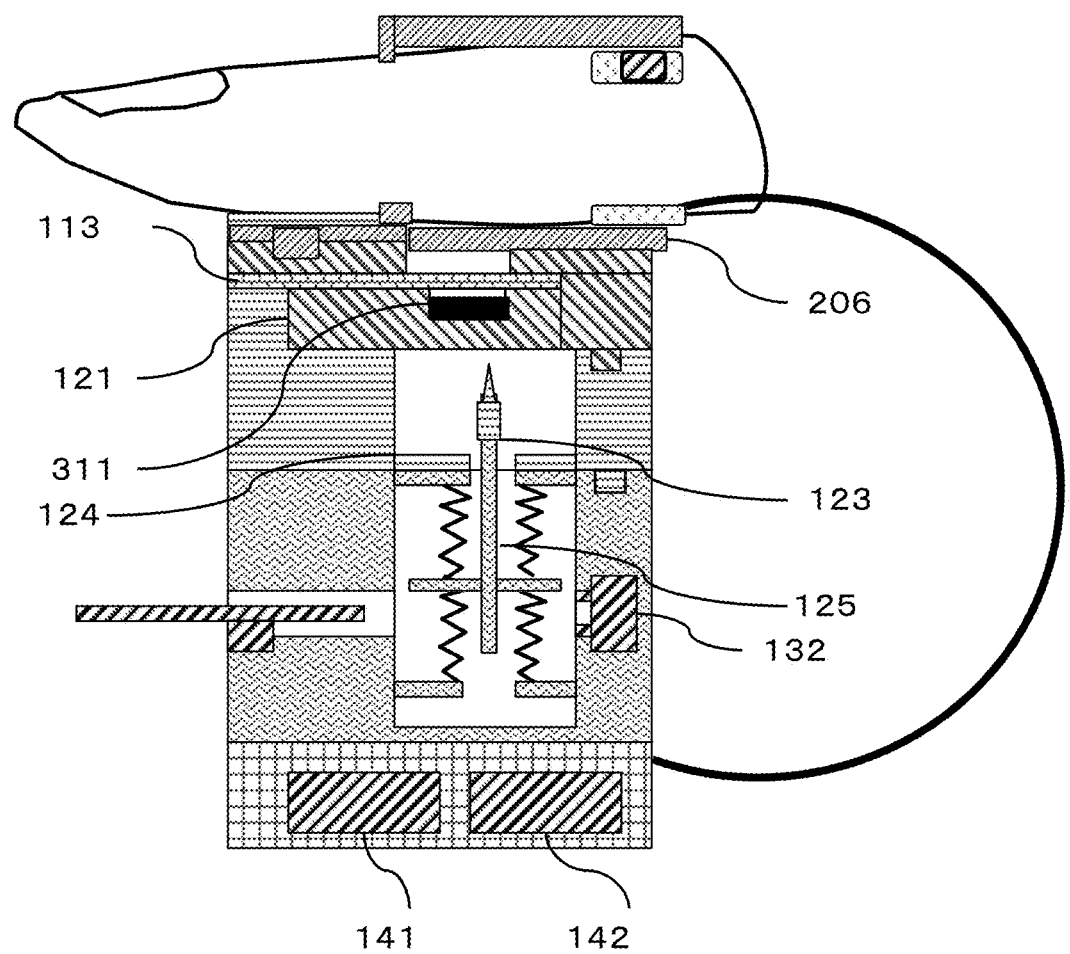

[Fig. 7B]
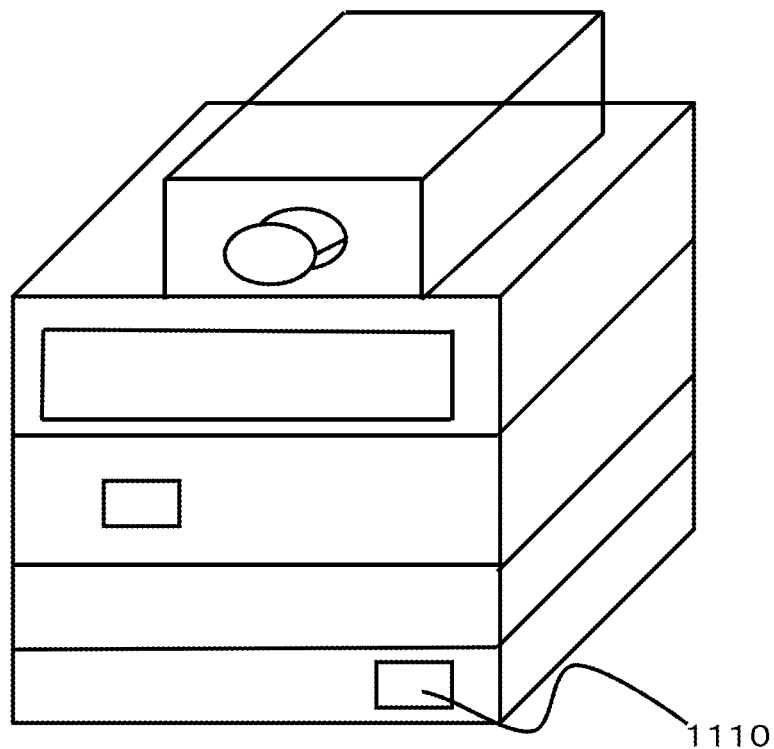

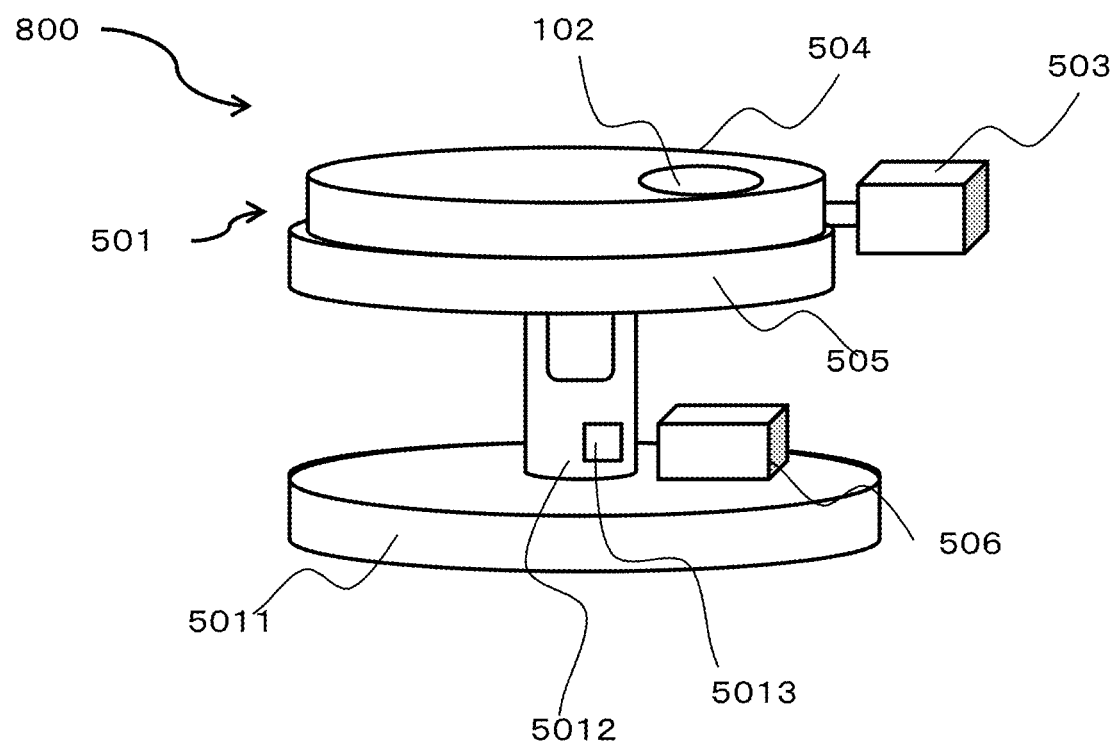
[Fig. 8A]

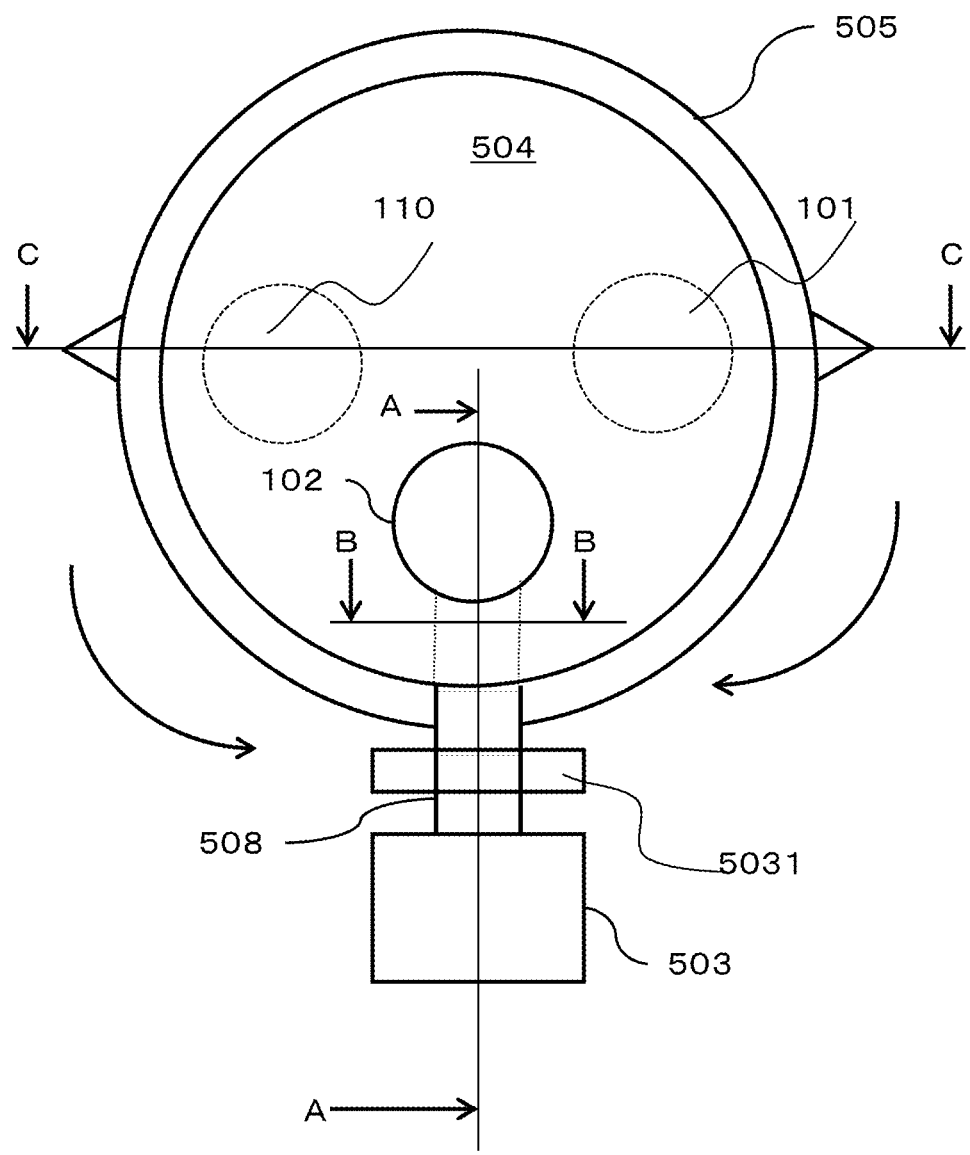
[Fig. 8B]

[Fig. 8C]
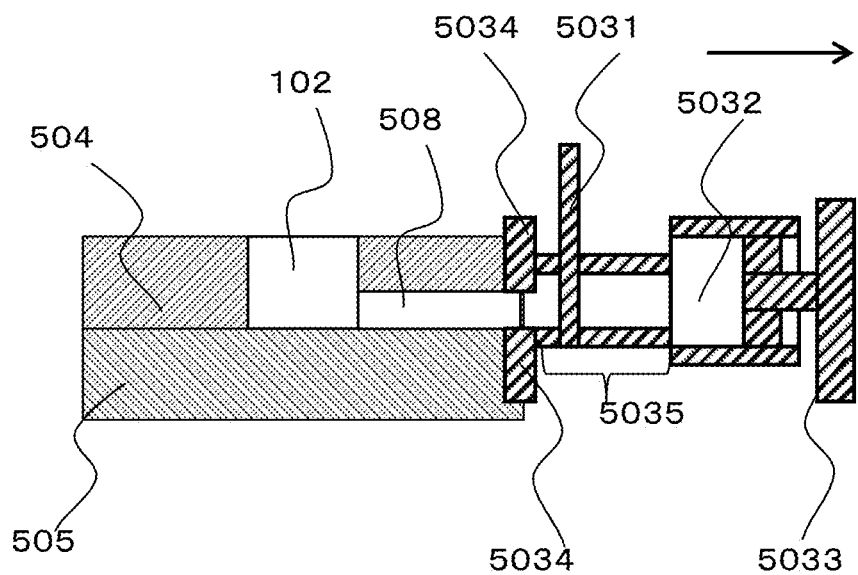
[Fig. 8D]
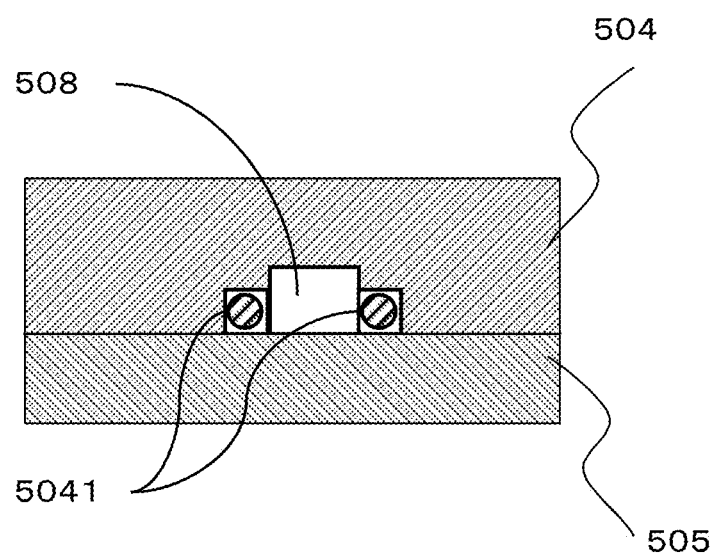

[Fig. 9]
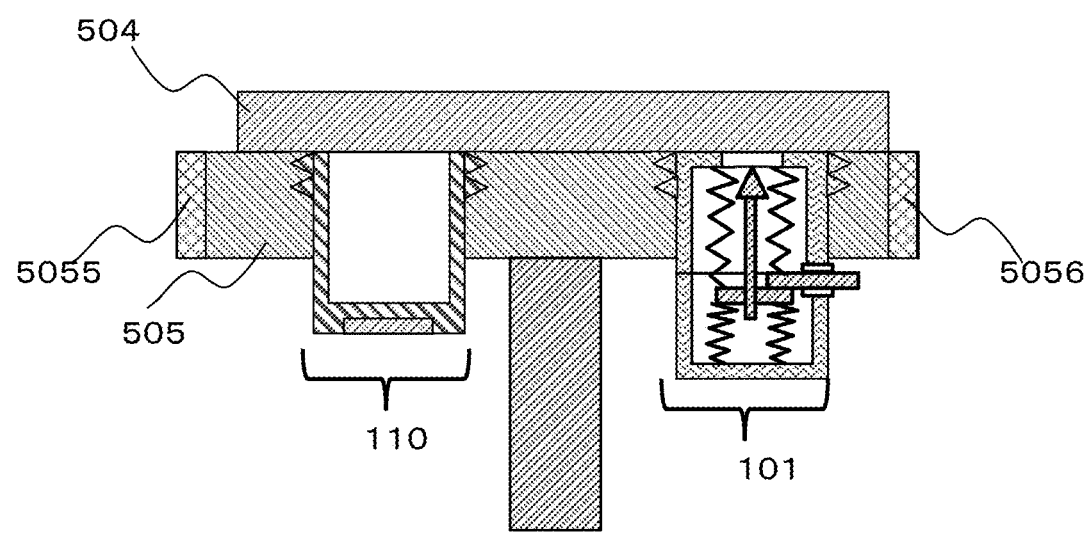

[Fig. 10]
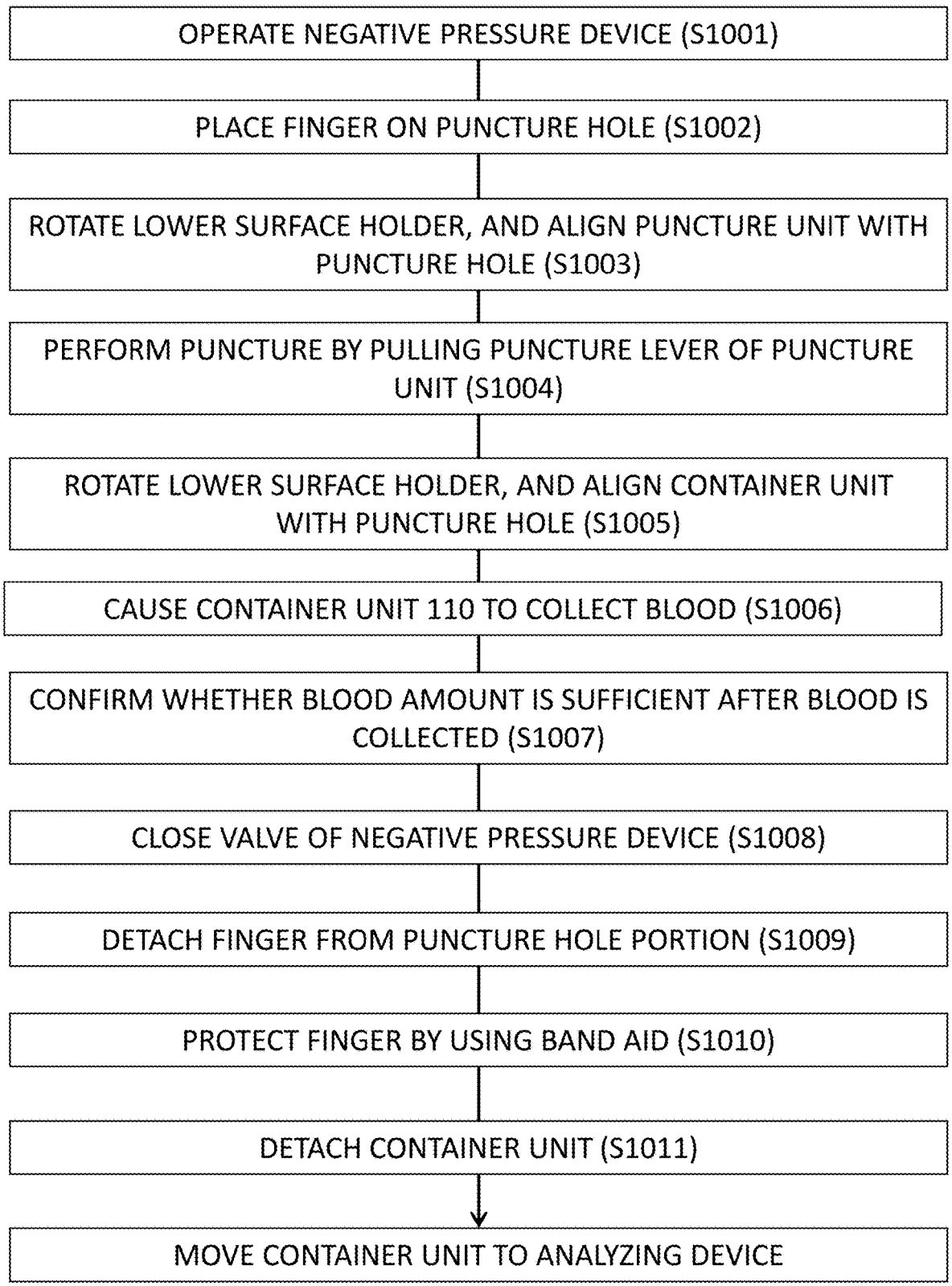

[Fig. 11A]
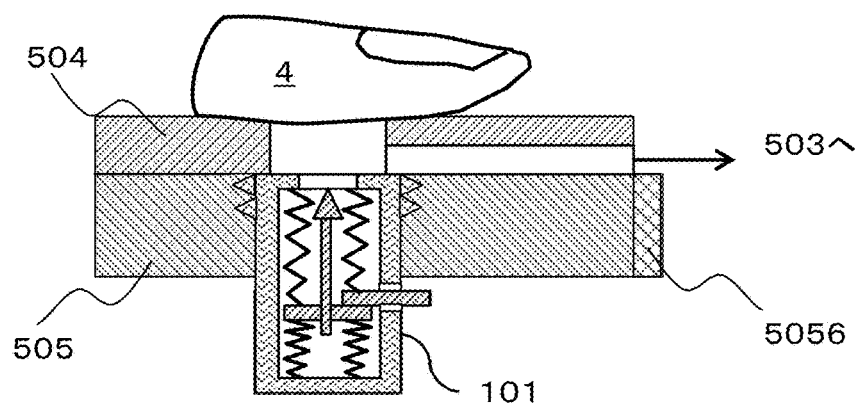
[Fig. 11B]
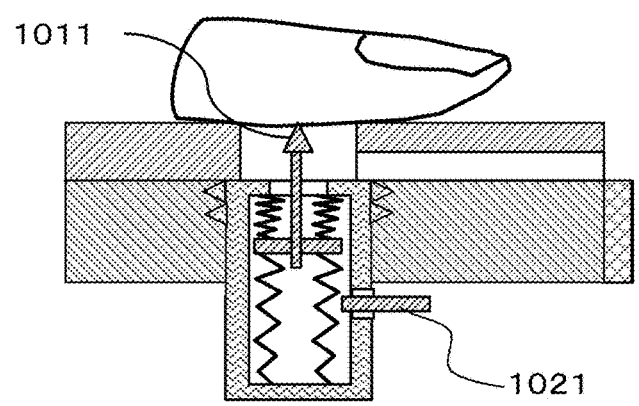
[Fig. 11C]
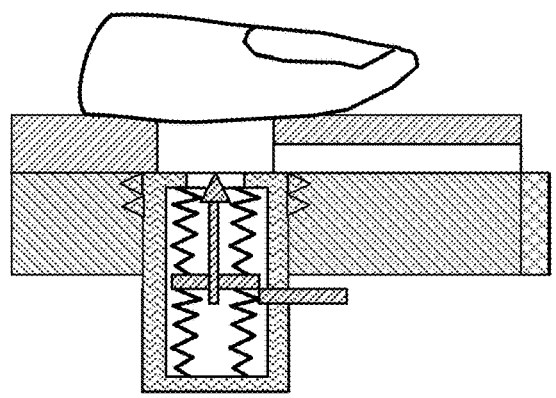

[Fig. 12A]
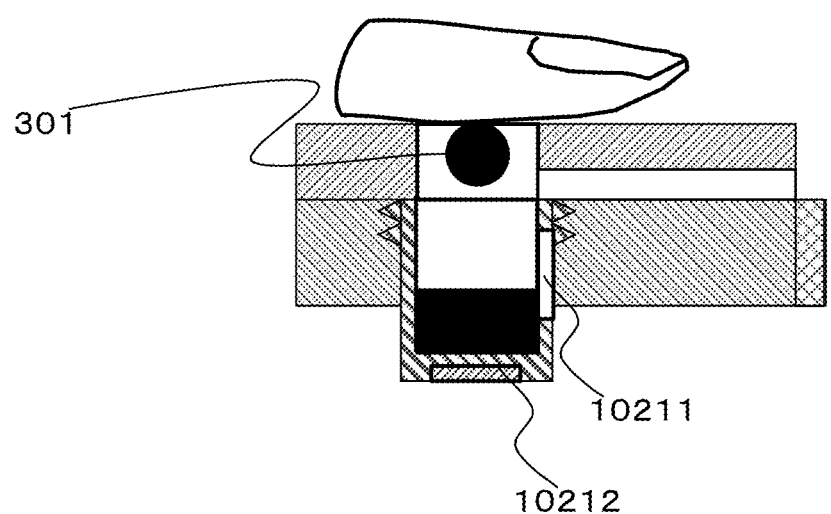
[Fig. 12B]
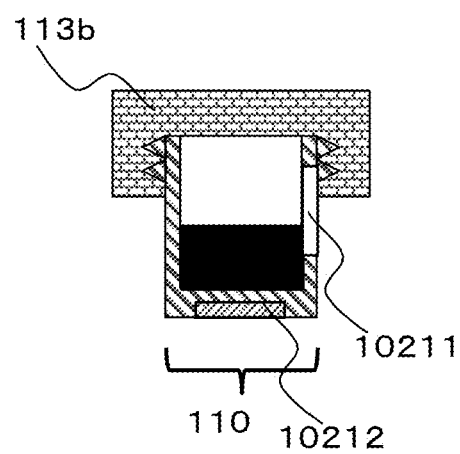

[Fig. 13A]
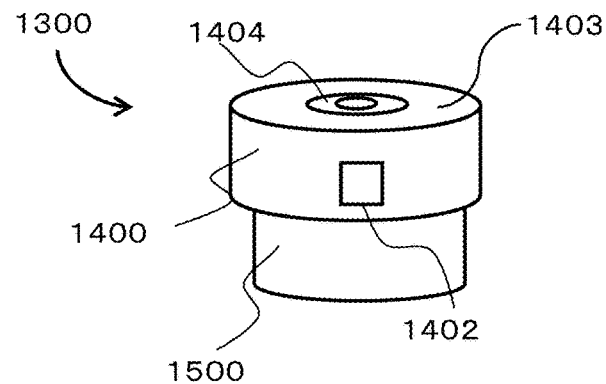
[Fig. 13B]
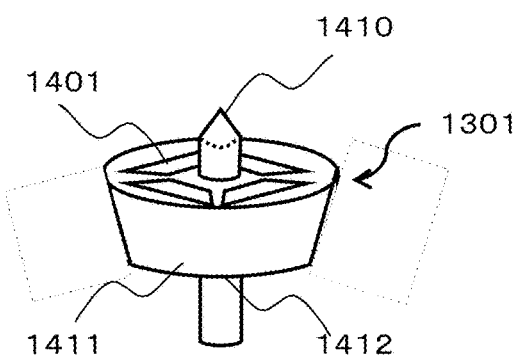
[Fig. 13C]
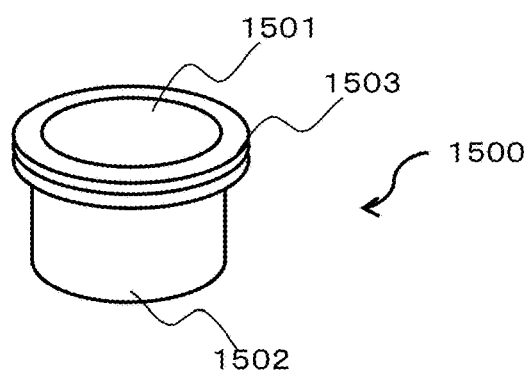

[Fig. 13D]
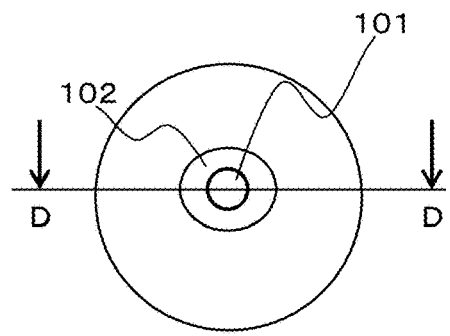
[Fig. 13E]
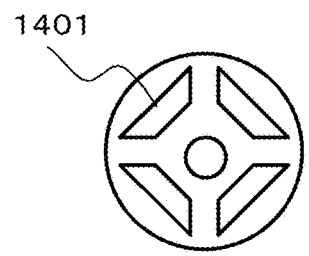
[Fig. 13F]
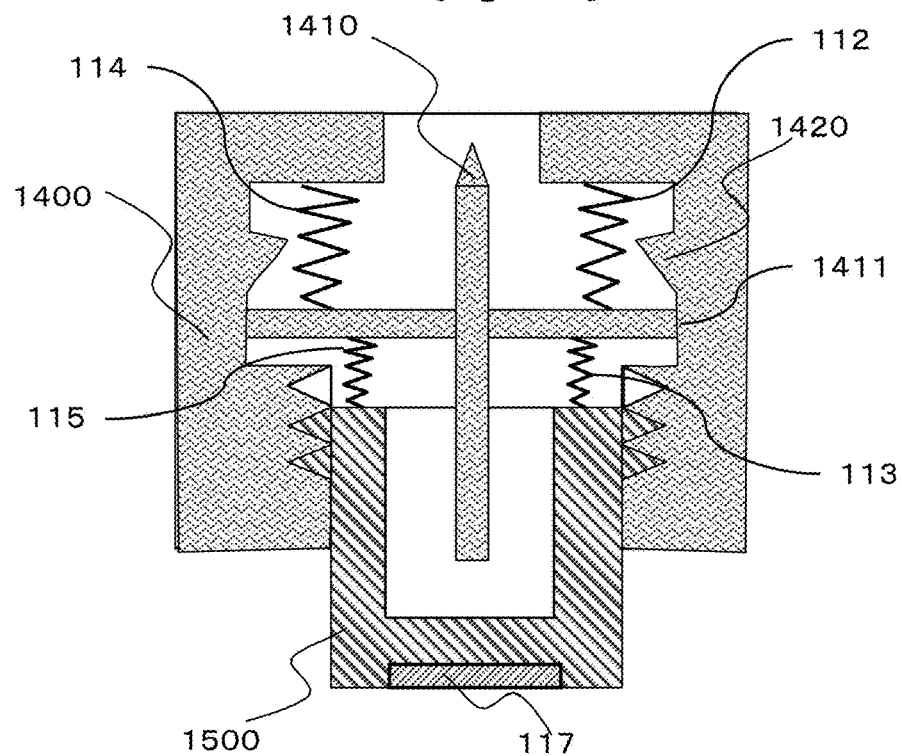

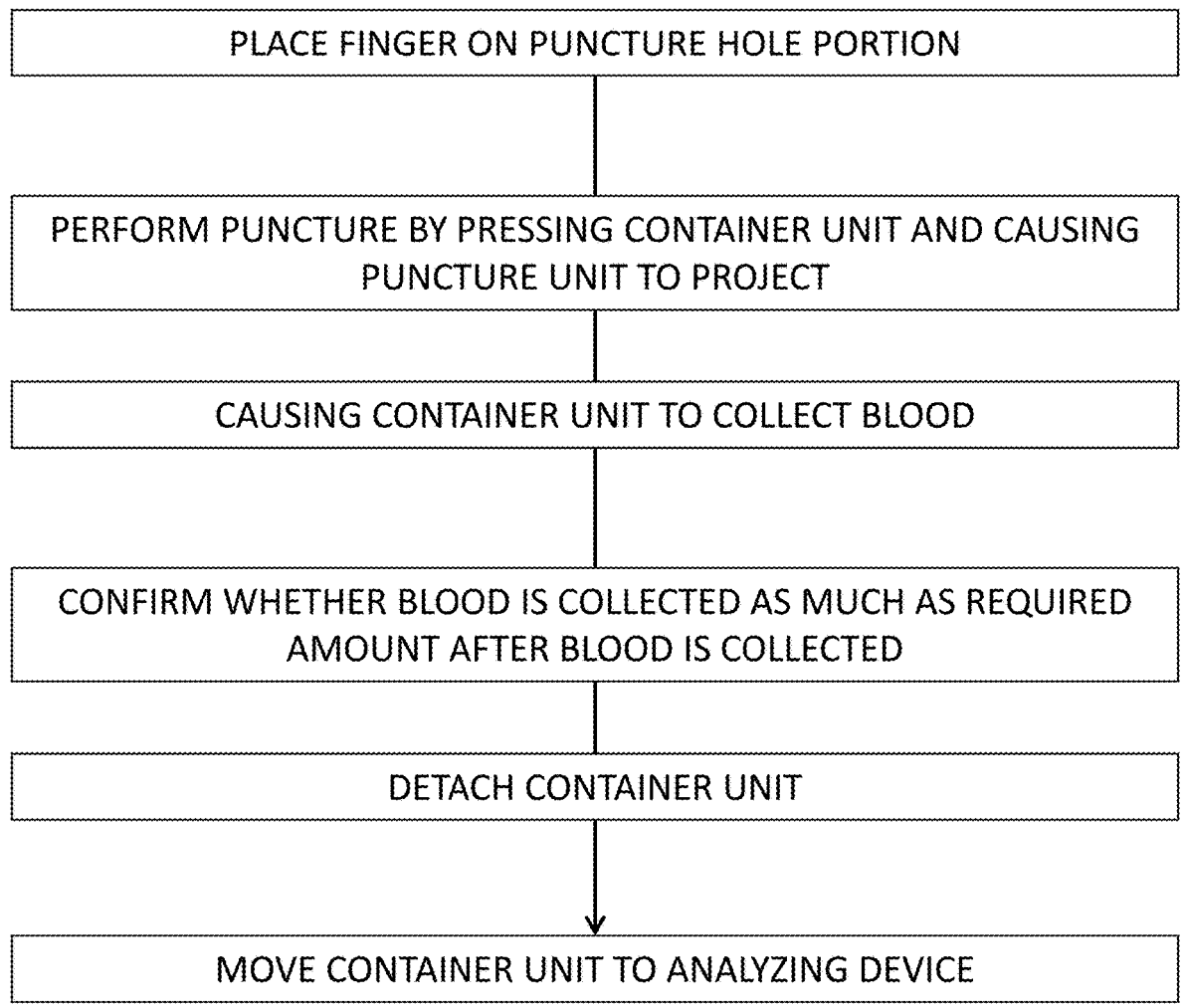
[Fig. 14]

[Fig. 15A]
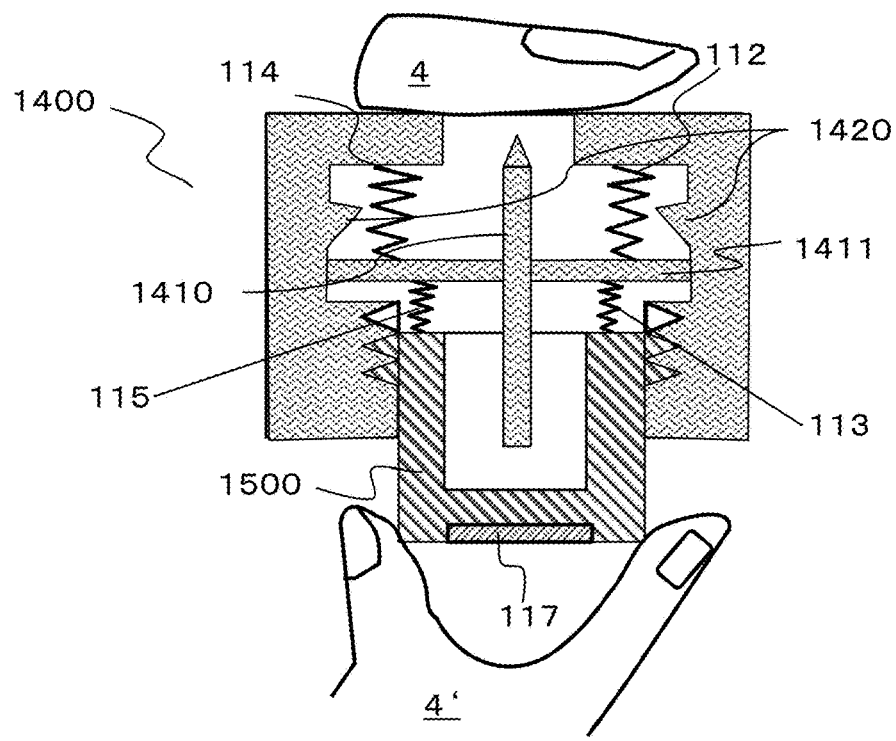
[Fig. 15B]
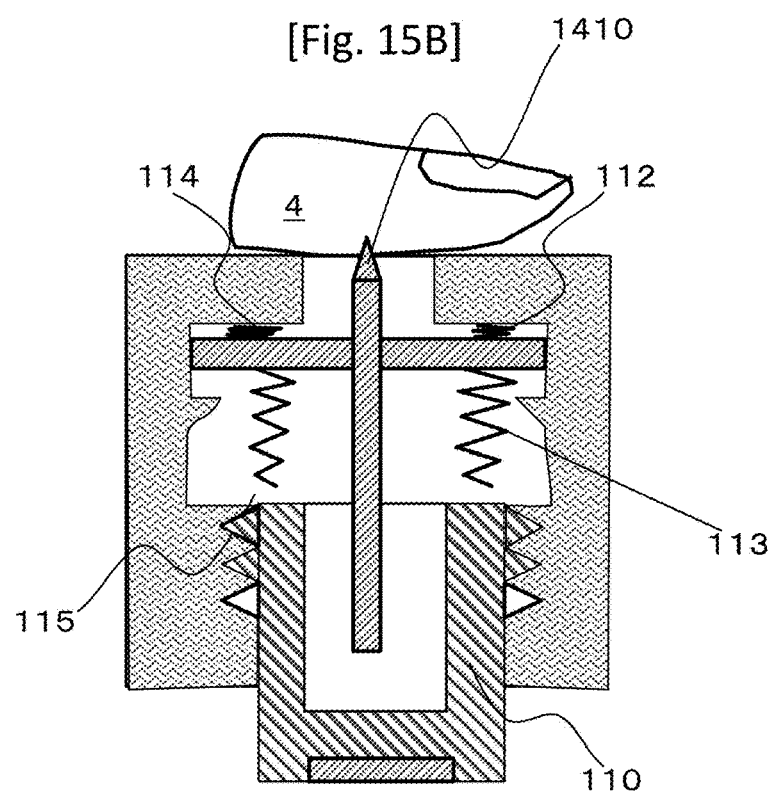

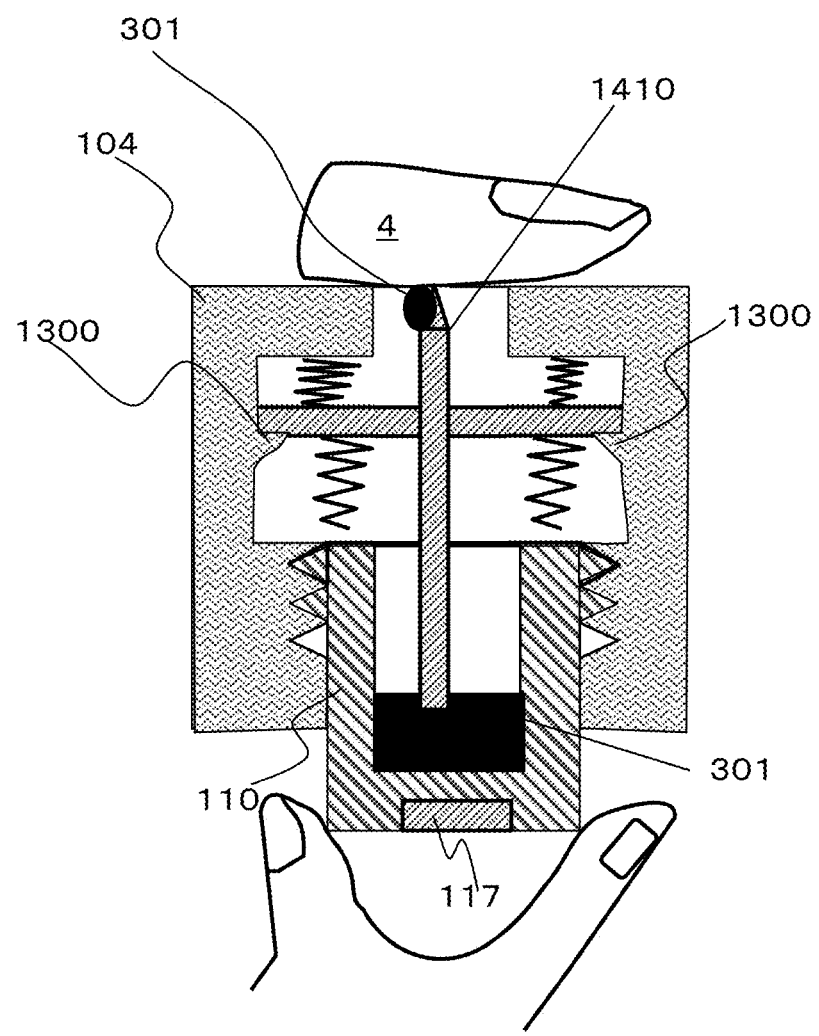
[Fig. 15C]

BLOOD COLLECTING DEVICE

TECHNICAL FIELD

The present invention relates to a blood collecting device.

BACKGROUND ART

PTL 1 (JP-A-7-213925) discloses a micro-volume blood collecting and spot application instrument which enables spot application in which a fixed amount of blood is applied to a predetermined inspection instrument. In addition, PTL 2 (JP-A-2002-219115) discloses a blood collecting device which can ensure a required blood amount in analyzing a specific component in body fluids in a short time, and which allows a painless blood collecting operation while avoiding a blood collecting failure.

CITATION LIST

Patent Literature

PTL 1: JP-A-7-213925
PTL 2: JP-A-2002-219115

SUMMARY OF INVENTION

Technical Problem

The blood collecting instrument disclosed in PTL 1 has a puncture/blood collecting tip formed of plastic which is less likely to be deformed. Consequently, a blood holder (blood aspirating passage) is less likely to aspirate blood. Therefore, it is difficult to collect the blood as much as (several tens to several hundreds of microliters) required for an inspection, and it is necessary to repeatedly perform puncture many times, thereby causing a problem in that a patient feels burdensome. In addition, the blood aspirating passage is open to the atmosphere. Consequently, the blood adheres to surrounding configurations, or the blood is scattered to open air, thereby causing a risk that a third party may be infected.

The blood collecting instrument disclosed in PTL 2 has the following problem. A blood flow is compressed in order to pressurize a blood collecting site after puncture is performed, and thus, the blood does not come out from the blood collecting site. Even if the blood comes out therefrom, it takes time to collect the blood. If it takes time to collect the blood, the puncture site is dried, and the constituent concentration in the blood is changed, thereby leading to poor inspection accuracy. In addition, if the blood collecting site is pressurized after the puncture is performed, the puncture site is dried during the pressurizing, thereby causing is a problem in that a sufficient amount of the blood cannot be collected.

An object of the present invention is to provide a blood collecting device capable of collecting blood in a short time after puncture is performed while the blood is not scattered to open air other than a container for collecting the blood.

Solution to Problem

In order to achieve the above-described object, the present invention is achieved as follows. One of representative blood collecting devices according to the present invention includes a container that has an opening portion and a closing portion in both ends, a holder that holds the opening portion of the container in a state where the opening portion faces upward, a fixing unit that fixes a blood collecting target in a state where the blood collecting target faces the opening portion, a pressure changing unit that pressurizes the blood collecting target or that applies negative pressure into a space surrounded by the blood collecting target and the container, a puncture unit that is attached to the container so as to be relatively movable, and that punctures the blood collecting target after pressure is changed by the pressure changing unit, and a lid that closes the opening portion of the container containing blood.

Advantageous Effects of Invention

According to the present invention, it is possible to provide a blood collecting device capable of collecting blood in a short time after puncture is performed while the blood is not scattered to open air other than a container for collecting the blood.

Objects, configurations, and advantageous effects other than those described above will be clarified from the description of the following embodiments.

BRIEF DESCRIPTION OF DRAWINGS

FIG. 1A is a view in which a finger is brought into contact with a blood collecting device and a fixing unit according to a first embodiment.

FIG. 1B is a perspective view illustrating the blood collecting device according to the first embodiment.

FIG. 1C is a sectional view illustrating a finger upper surface fixing member of the blood collecting device according to the first embodiment.

FIG. 1D is a sectional view illustrating a finger lower surface fixing member of the blood collecting device according to the first embodiment.

FIG. 1E is a sectional view illustrating the fixing unit of the blood collecting device according to the first embodiment.

FIG. 2 is a view illustrating a process of the blood collecting device according to the first embodiment.

FIG. 3A is a view illustrating a puncture process of the blood collecting device according to the first embodiment.

FIG. 3B is a perspective view illustrating the puncture process of the blood collecting device according to the first embodiment.

FIG. 4A is a view illustrating when a needle projects in the puncture process of the blood collecting device according to the first embodiment.

FIG. 4B is a perspective view illustrating when the needle projects in the puncture process of the blood collecting device according to the first embodiment.

FIG. 5 is a view illustrating after the blood collecting device according to the first embodiment performs puncture.

FIG. 6A is a view illustrating a blood collecting process of the blood collecting device according to the first embodiment.

FIG. 6B is a perspective view illustrating the blood collecting process of the blood collecting device according to the first embodiment.

FIG. 7A is a view illustrating a process of protecting a puncture site according to the first embodiment.

FIG. 7B is a perspective view illustrating the process of protecting the puncture site according to the first embodiment.

FIG. 8A is a perspective view of a blood collecting device according to a second embodiment.

FIG. 8B is a top view of the blood collecting device according to the second embodiment.

FIG. 8C is a sectional view illustrating a cross section of a holder and a negative pressure device of the blood collecting device according to the second embodiment.

FIG. 8D is a sectional view illustrating a cross section of the blood collecting device according to the second embodiment.

FIG. 9 is a view illustrating a cross section of the blood collecting device according to the second embodiment.

FIG. 10 is a view illustrating a process of the blood collecting device according to the second embodiment.

FIG. 11A is a view illustrating a puncture process of the blood collecting device according to the second embodiment.

FIG. 11B is a perspective view illustrating when a needle projects in the puncture process of the blood collecting device according to the second embodiment.

FIG. 11C is a view illustrating after the blood collecting device according to the second embodiment performs puncture.

FIG. 12A is a view illustrating a blood collecting process of the blood collecting device according to the second embodiment.

FIG. 12B is a view illustrating a container unit after the blood collecting device according to the second embodiment performs the puncture.

FIG. 13A is a perspective view of a blood collecting device according to a third embodiment.

FIG. 13B is a perspective view of a puncture unit of the blood collecting device according to the third embodiment.

FIG. 13C is a perspective view of a container unit of the blood collecting device according to the third embodiment.

FIG. 13D is a perspective view of the container unit and the puncture unit of the blood collecting device according to the third embodiment.

FIG. 13E is a top view of the blood collecting device according to the third embodiment.

FIG. 13F is a view illustrating a cross section of the blood collecting device according to the third embodiment.

FIG. 14 is a view illustrating a process of the blood collecting device according to the third embodiment.

FIG. 15A is a view illustrating a puncture process of the blood collecting device according to the third embodiment.

FIG. 15B is a view illustrating the puncture process of the blood collecting device according to the third embodiment.

FIG. 15C is a view illustrating a blood collecting process of the blood collecting device according to the third embodiment.

DESCRIPTION OF EMBODIMENTS

Hereinafter, embodiments according to the present invention will be described with reference to the drawings.

First Embodiment

FIGS. 1A and 1B illustrate a structure of a blood collecting device according to a first embodiment. FIG. 1A is a sectional view, and FIG. 1B is a perspective view.

In the blood collecting device according to the present invention, a fixing unit 2 for fixing a finger 4 is provided on a blood collecting device 1 in which a movable container unit 110, a movable puncture unit 120, a drive fixing unit 130, and a drive unit 140 are integrally combined with each other.

The movable container unit 110 includes a container 112 for containing the blood collected from the finger 4. The volume of the blood which can be contained inside the container 112 varies depending on the application. However, according to the method of the present embodiment, a relatively large volume (approximately, several tens to several hundred microliters) of the blood can be collected to the maximum. The opening portion which receives the blood in the container 112 is provided with a movable lid 113, and is configured to be openable and closeable. The container 112 itself is configured to be manually movable relative to the movable container unit 110 in the horizontal direction. A movable range of the container 112 is limited by a guide mechanism 113 and a positioning mechanism 1014. In order to couple the fixing unit 2 and the movable puncture unit 120 with each other, a groove capable of engaging with a projection portion 208 disposed in the fixing unit 2 and a projection portion 111 projecting to the movable puncture unit 120 are disposed therein.

The movable puncture unit 120 is connected to the movable container unit 110, and internally has a needle tip 122, a needle portion connector 123, and a needle holder 124. The needle tip 122 is initially fixed to the needle holder 124. However, the needle tip 122 is connected to a drive fixing unit (to be described later). In this manner, the needle tip 122 is attached to a tip of a shaft 125 disposed inside the drive fixing unit, and is removed from the needle holder 124. Therefore, it is preferable that the needle portion 123 and the needle holder 124 are connected to each other so that both of these can be separated from each other using a weak force. The needle tip 122 and the shaft 125 are detachably connected to each other using the needle portion connector 123. The needle tip 122 and the shaft 125 can be separated from each other if a blood collecting process is completed. If the needle connector 123 is connected to the detachable the shaft 125, the needle connector 123 and the needle holder 124 disengage from each other, and the movable puncture unit 120 and the drive fixing unit 130 are connected to each other.

The drive fixing unit 130 includes a spring accommodating portion 131 connected to the movable puncture unit 120 and having a needle connected to a spring, and a pressure source 132 for applying pressure into the spring accommodating portion 131. In the present embodiment, the pressure source 132 serves as a negative pressure source for generating negative pressure. In addition, the shaft 125 detachable from the needle tip 122, and four springs, one end of which is fixed to the rib of the shaft and the other end of which is fixed to the drive fixing unit 130, are disposed inside the spring accommodating portion 131. Furthermore, a puncture portion fixing unit 133 which is slidable for fixing a position of the needle portion by coming into contact with the rib of the shaft is disposed therein.

The drive unit 140 is connected to the fixing unit 2 (to be described later), and includes a sphygmomanometer 141 and a pressurizing device 142. The pressurizing device 142 feeds air to a compression body 203 around a finger (to be described later), and the sphygmomanometer 141 receives pressure information from a pressure gauge 207 disposed in the compression body 203. In addition, the drive unit 140 includes a drive switch 143 for controlling the driving of the pressurizing device 142.

The fixing unit 2 is formed from a finger upper surface fixing member 201, a finger lower surface fixing member 202, a finger fixing holder 205, a pneumatic compression body 203 disposed around a finger body, and a movable lower surface holder 206. The finger upper surface fixing member 201 and the finger lower surface fixing member 202 need to maintain airtightness to some degree by coming into contact with the finger 4. Accordingly, it is preferable to use a resin member or an elastic member. The compression body 203 disposed around the finger body is expanded, thereby causing the puncture site of the finger 4 to be sealed with the finger upper surface fixing member 201, the finger lower surface fixing member 202, and the compression body 203. Preferably, the fixing unit 2 is provided with a blood pressure sensor 207, and a blood pressure value is measured while the finger is compressed with the compression body 203. The fixing unit communicates with the sphygmomanometer 141 of the drive unit 140 via a connecting body 3 such as a wire. Furthermore, the compression body 203 is connected to the pressurizing device 142 of the drive unit 140.

As illustrated in FIG. 1C, the finger upper surface fixing member 201 includes a fixing portion 2011 and an elastic member 2012, and the elastic member 2012 comes into close contact with the finger. Similarly, FIG. 1D illustrates the finger lower surface fixing member 202, which has the configuration the same as that of the finger upper surface fixing member 201. FIG. 1E illustrates a state where the finger upper surface fixing member 201 and the finger lower surface fixing member 202 are combined with each other. The elastic member 2012 comes into close contact with the finger so as to cover the entire circumference of the finger, thereby preventing the position of the finger from being misaligned during the blood collection, and sealing a puncture hole portion 209 through which the blood is actually collected. It is not necessary to completely seal the puncture hole portion 209 as long as the pressure inside the puncture hole portion 209 can be maintained lower than at least the blood pressure while at least the blood is collected. In addition, the fixing unit 2 may be disposed so as to entirely cover the finger.

In the above-described blood collecting device, there is a possibility that the movable container unit 110 and the movable puncture unit 120 may come into contact with the blood. Accordingly, both of these are replaced every time the blood is collected. On the other hand, the fixing unit 2, the drive fixing unit 130, and the drive unit 140 are less likely to come into contact with the blood. Accordingly, all of these do not need to be replaced every time the measurement is performed. All of these can be repeatedly used. Therefore, it is preferable that the fixing unit 2, the movable container unit 110, the movable puncture unit 120, and the drive fixing unit 130 are all assembled so as to be disassembled. The fixing unit 2 and the movable container unit 110 can be connected to each other by engaging a projection 208 belonging to the fixing unit 2 with the movable container unit 110. Similarly, the movable container unit 110 and the movable puncture unit 120 are connected to each other using a projection 111 belonging to the movable container unit 110. The movable puncture unit 120 and the drive fixing unit 130 are connected to each other using a projection 121 of the movable puncture unit 120. When the movable puncture unit 120 and the fixing drive unit 130 are connected to each other, an operator positions the rib of the shaft by using a puncture portion fixing unit 133 of the fixing drive unit 130. In this state, the operator attaches the needle connector 123 to the tip of the shaft.

An algorithm in a case where the blood is collected using the blood collecting device according to the first embodiment will be described with reference to FIGS. 2 to 7.

First, in a state where the finger 4 is inserted into an insertion hole disposed in the fixing unit 2, a drive switch 143 of the drive unit 140 is pressed (Step 301). In this case, the pressurizing device 142 is operated, and the compression body 203 around the finger tightens the finger 4 (Step 302). Then, the blood pressure of the finger 4 is monitored by an output of the pressure sensor 207 when the compression body 203 around the finger tightens the finger 4, and the monitored blood pressure is transmitted to the sphygmomanometer 141 of the drive unit 140. After the highest blood pressure is measured by the sphygmomanometer 141, the lowest blood pressure is measured in such a way that the pressurizing device 142 reduces the pressure inside the compression body 203 around the finger. A method of calculating the highest blood pressure and the lowest blood pressure may be the same as the method of using the sphygmomanometer in the related art (Step 303).

Thereafter, the inside of the compression body around the finger is pressurized by the pressurizing device so that the pressure is set to be in a range of the highest blood pressure to the lowest blood pressure (Step 304). Since the pressure is set to be in the range of the highest blood pressure to the lowest blood pressure, the blood flow is not stopped due to excessive tightening. Therefore, it is possible to encourage bleeding when the puncture is performed by applying moderate pressure.

If the pressure inside the compression body around the finger reaches a pressure value falling within a proper range, a blood collector moves the container 112 of the movable container unit 110 so as to pull out the container 112 of the movable container unit 110 (Step 305). The blood collecting device in this state is illustrated in FIGS. 3A and 3B. A guide mechanism 1013 configured to include a rail is disposed on a side surface of the container 112, and the container 112 can be pulled out along the rail. In addition, the maximum amount of movement which can be pulled out is controlled by a positioning mechanism 1014.

The movement of the container 112 provides a mutually connected space for the puncture hole portion 102 and the spring accommodating portion 131. If the negative pressure device 1032 is driven in this state, the spring accommodating portion 1031 and the puncture hole portion 102 are internally brought into a negative pressure state. If the puncture is performed, the differential pressure causes the blood to easily flow out of the finger 4 (Step 306). The negative pressure device 132 is driven by pressing the drive switch 143.

After the puncture hole portion 209 is brought into the negative pressure state, the movable puncture unit 120 is moved. The movable puncture unit 120 detaches and manually pulls the puncture portion fixing unit 133 out of the positioning portion 134 of the puncture portion fixing unit 133. Then, as illustrated in FIG. 4, the springs 112 to 115 fixing the needle tip 122 expand and contract, and the needle portion projects to the finger so as to puncture the finger 4 (Step 307). After the finger is punctured, all of the springs restore each natural length as illustrated in FIG. 5, and the needle tip 122 is separated from a puncture site.

Thereafter, as illustrated in FIG. 6, the container 112 is moved so as to be disposed directly below the puncture site, and leaking blood 301 is contained in the container 112 (Step 308). It is preferable to adopt a configuration in which the container 112 is formed of a transparent resin, and in which a blood collecting degree of the blood 301 is visible from the outside. In addition, if necessary, a memory may be disposed in order to confirm whether a sufficient amount of the blood is completely collected.

After a predetermined amount of the blood collected in the container unit (Step 309), the pressure inside the compression body around the finger is reduced by the pressurizing device. Since the pressure of the compression body around the finger is reduced, the blood starts to flow from a vein of the pressurized finger, and the scar of the puncture site on the finger is closed, thereby preventing unnecessary bleeding (Step 310).

Thereafter, the lid 113 of the container unit is moved so as to close the opening portion of the container. In addition, in order to protect the puncture portion of the finger, the lower surface holder 206 is moved below the puncture portion of the finger, and the puncture portion is protected (Step 311, FIG. 7A). Thereafter, the movable container unit 101 is detached from the fixing unit 2 and the movable puncture unit 103 (Step 312). When detached, the opening portion of the container 112 is closed by the lid 113. Accordingly, it is possible to prevent the collected blood from being scattered to the surroundings. The collected blood can be fed to an analyzing device which can quantitatively and qualitatively analyze blood components for each movable container unit 110.

In the first embodiment, the compression body 203 and the negative pressure source 132 are provided. In this manner, even if a relatively large amount of the blood is collected, it does not take much time. In addition, without repeatedly performing the puncture process many times, it is possible to collect the blood.

Furthermore, as another advantageous effect of the present invention, the movable lid is disposed in the container for containing the collected blood. Therefore, when the blood is delivered or stored after the blood is collected, it is possible to reduce the risk that the blood may spill and contaminate the surroundings or that the collected blood may be mixed with bacteria floating in the open air.

Furthermore, as another advantageous effect of the present invention, a proper range of compression amount is applied to the finger by the compression body 203 before the puncture process is performed. Accordingly, if the finger is decompressed by the compression body 203, bleeding is less likely to occur from the puncture portion (scar), and it is possible to reduce the risk that the surroundings may be contaminated due to the bleeding from the scar after the blood collecting process is performed.

Furthermore, as another advantageous effect of the present invention, a configuration is adopted in which a repeatedly usable mechanism can be separated from or combined with a mechanism to be replaced for a single blood collecting process. Therefore, it is possible to reduce the cost required for blood collecting process.

Second Embodiment

Next, a second embodiment according to the present invention will be described with reference to FIGS. 8 to 12. The second embodiment is different from the first embodiment in that an upper disk 504 having the puncture hole 102 for pressing the finger and a lower disk having the container unit 110 and the puncture unit 101 are arranged one above the other. In the present embodiment, the fixing unit for fixing the finger to the puncture hole 102 is omitted. However, a configuration similar to that of the fixing unit 2 according to the first embodiment may be provided on the puncture hole portion 102 of a holder 501.

FIG. 8A illustrates a perspective view of a blood collecting device 800 according to the second embodiment. The blood collecting device 800 includes a disk 501, a negative pressure device 503, a holder supporting body 5011 for supporting the disk, and a lower surface holder supporting body 5012. In addition, the blood collecting device 800 may include a blood collecting amount confirmation mechanism 506 for confirming the blood collecting amount. For example, the blood collecting amount confirmation mechanism 506 may adopt any configuration such as a pressure gauge and an optical sensor as long as the blood collecting amount can be measured within the range of the related art.

The disk 501 includes an individually rotatable upper disk 504 and a lower disk 505. The upper disk includes at least one puncture hole 102 for pressing a puncture target finger. In addition, the lower disk has at least one container unit 110 and one puncture unit 101. The lower disk is rotated, thereby enabling positions of both the units to be switched therebetween.

FIG. 8B illustrates a top view of the holder 501 in FIG. 8A. The lower disk 505 and the upper disk 504 are concentrically arranged, and the lower disk 505 is configured to be slightly larger. The upper disk 504 has at least one puncture hole 102, and the negative pressure device 503 is connected to the puncture hole 102 via a negative pressure flow path 508. Levers 5055 and 5056 (to be described later) are disposed in the lower disk 505. The lower disk 505 can be manually rotated clockwise and counterclockwise by gripping the levers.

FIG. 8C illustrates a cross section taken along line A-A in FIG. 8B. The puncture hole 102 and the negative pressure flow path 508 are formed on the upper disk 504 side. The negative pressure flow path 508 is formed by digging a groove on a lower surface of the upper disk 504. The negative pressure device 503 is connected to the negative pressure flow path 508 by using a connector 5034, a flow path 5035, and an openable/closeable valve 5031. In addition, the negative pressure device 503 includes a pressure unit 5032 and a plunger 5033. If the negative pressure device 503 closes the valve 5031 and pulls the plunger 5033, the pressure unit 5032 is brought into a negative pressure state. Thereafter, the valve 5031 is opened by placing the finger on the puncture hole portion 102, the negative pressure flow path 508 and the flow path 5035 are connected to each other, thereby enabling the puncture hole portion 102 to be brought into the negative pressure state. The plunger may be moved manually or using a machine such as a motor.

FIG. 8D illustrates a cross section taken along line B-B in FIG. 8B. The upper disk 504 and the lower disk 505 are sealed with an O-ring 5041 so as not to have a gap therebetween.

FIG. 9 illustrates a cross section taken along line C-C in FIG. 8B. The container unit 110 and the puncture unit 101 are in a state where both of these are attached to the lower disk 505. The container unit 110 and the puncture unit 101 are exchanged each time the blood is collected. However, other structures such as the disk 501 are repeatedly used. Therefore, it is preferable to adopt a configuration in which the container unit 110 and the puncture unit 101 have a cylindrical outer shape and are be attachable to and detachable from the lower disk 505 by using screw holes. The lower surface holder 505 is rotatable as illustrated in FIG. 8B. In a case where the lower surface holder 505 is manually moved, the lower surface holder 505 is rotated by gripping the levers 5055 and 5056.

In a case where the lower surface holder 505 is automatically moved, a motor for driving the lower disk is incorporated in the holder supporting body 5011 and the lower surface holder supporting body 5012. Accordingly, a drive button 5013 (illustrated in FIG. 8A) of the lower surface holder supporting body 5012 may be pressed so as to rotate the lower surface holder 505.

An algorithm of the operation of the blood collecting device 800 will be described with reference to FIGS. 10 and 11. FIG. 11 illustrates a change in a structure of the cross section taken along line B-B in FIG. 8B. Referring to FIG. 11, a structure of the negative pressure device 503 is omitted.

In the present embodiment, the negative pressure device 503 is first operated before the finger is fixed (Step 1001). In order to drive the negative pressure device 503, the valve 5031 is closed. If the plunger 5033 is pulled, the pressure unit 5032 is internally brought into a negative pressure state.

Thereafter, the finger 4 is placed on the puncture hole portion 102 (Step 1002), the valve 5031 is opened, the negative pressure flow path 508 and the flow path 5035 are connected to each other, and a space between the puncture hole portion 102 and the finger is brought into a negative pressure state.

Thereafter, the lever 5055 and the lever 5056 are gripped, and the lower surface holder 505 is rotated so that the puncture unit 101 is positioned below the puncture hole portion 102 as illustrated in FIG. 11A (Step 1003). If movement angles can be aligned by adjusting the position of the lever 5056 and the position of the flow path 5035, the burden of alignment is reduced.

In this state, if a puncture lever 1021 disposed in the puncture unit 101 is pulled, the needle 1011 projects (Step 1004, a state of FIG. 11B). Thereafter, the needle 1011 returns to the inside of the puncture unit 101 due to a biasing force of the spring (state of FIG. 11C).

Thereafter, in order to position the container unit 110 below the puncture hole portion 102, the lower disk is rotated, and the lever 5055 illustrated in FIG. 9A is aligned with the flow path 5035 (Step 1005, a state of FIG. 12A). The container unit 110 is placed in this state. In this manner, due to the influence of the negative pressure, the blood 301 bleeding from the puncture scar is accumulated inside the container of the container unit 110 (Step 1006).

The blood collecting amount confirmation mechanism 506 confirms that the blood 301 inside the container is collected as much as the required amount (Step 1007). A confirming method of the blood collecting amount confirmation mechanism 506 may be visually performed. In addition, a small mirror 115 may be disposed at a place where a memory is marked on a side wall of the container unit 110, and the mirror 116 may be disposed below the container unit 110. In this manner, light or laser may be emitted from the blood collecting amount confirmation mechanism 506, and the blood collecting amount may be measured by monitoring the blood collecting amount with a camera.

After the blood is collected as much as the required amount, the valve 5031 (illustrated in FIG. 8(C)) of the negative pressure device 503 is closed (Step 1008), and the finger 4 is detached from the puncture hole portion 102 (Step 1009). A protective tape such as a protecting band aid adheres to the puncture scar of finger 4 (Step 1010). Thereafter, the container unit 110 is detached from the holder 501 (Step 1011), and the collected blood is delivered to an analyzer or a centrifuge if necessary. The container unit 110 may be covered with a lid 113b as illustrated in FIG. 12B before the container unit 110 is delivered.

According to the present embodiment, the puncture unit 101, the container unit 110, and the puncture hole portion 102 are present on the same plane by using the rotatable holder 501. Accordingly, the puncture site, the puncture unit 101, and the container unit 110 can be accurately aligned with each other in a short time, and the blood can be collected as much as the required amount in a short time.

The holder 501 includes the upper surface holder 504 and the lower surface holder 505. Accordingly, after the puncture is performed, the blood 301 does not contaminate the holder supporting body 5011, the lower surface holder supporting body 5012, and the blood collecting amount confirmation mechanism 506. Therefore, the blood is less lost, and the blood can be collected as much as the required amount in a short time.

Third Embodiment

Next, a third embodiment according to the present invention will be described with reference to FIGS. 13 to 15.

In the third embodiment, as illustrated in FIGS. 13 to 15, a puncture unit 1400 and a container 1500 are integrated with each other, and a blood collecting device 1300 having a through-hole 1401 in the puncture unit 1400 is provided. This point is changed compared to a case according to the first embodiment.

FIG. 13A is a perspective view of the blood collecting device 1300. The blood collecting device 1300 has a configuration in which the puncture unit 1400 and the container 1500 are assembled by being stacked one above another. A small transparent confirmation window 1402 is disposed on a side surface of the puncture unit 1400, and a blood collecting state of the blood is visibly confirmed. An adhesive member 1403 such as a double-sided adhesive tape adheres to at least a portion of an outer wall of the puncture unit 1400. The adhesive member adhering to the puncture side has an adhesive force which does not allow the finger to move and which allows the finger to be easily detached therefrom. The puncture unit side may be formed of an elastic member. A configuration may be adopted in which the finger and a puncture hole portion 1404 are likely to be in close contact with each other. The finger is fixed using the double-sided adhesive tape. Therefore, it is possible to reduce the risk that the blood may stick to the surroundings after the finger is deviated from the puncture unit during the blood collection process.

FIG. 13B is a perspective view of a structure inside the puncture unit 1400. The puncture unit 1400 includes a needle 1410, and includes a plurality of through-holes 1401, a puncture rib 1411, and a puncture unit supporting portion 1412 below the needle 1410. The through-holes 1401 are arranged so as to form a hole as large as possible around the needle 1410. The finger is punctured using the needle 1410. When the puncture unit 1400 and the container 1500 are connected to each other, the puncture unit 1400 is located so as to reach an open end side of the container 1500.

FIG. 13C is a perspective view of the container 1500. The container 1500 has an open end 1501, a closed end 1502, and a container screw portion 1503. The blood flows from the open end 1501 side, and the blood is accumulated in the closed end 1502. A bottom surface of the closed end 1502 includes a collected blood confirmation portion 117 (refer to FIG. 13E).

FIG. 13D is a top view of the blood collecting device 1300, and FIG. 13E is a top view of the puncture unit 101 from which the puncture drive unit 104 of the blood collecting device 3 is removed. FIG. 13F illustrates a cross section taken along line D-D in FIG. 13D. The puncture unit 1400 internally includes springs 112 to 115 and a projection portion 1420. The puncture unit 1400 and the container 1500 are detachably connected to each other using a container screw portion 109.

The needle 1410 having the puncture rib 1411 is accommodated in the puncture unit 1400. One end of the spring 113 and the spring 115 is connected to a lower surface of the puncture rib 1411. The other end of the springs is in contact with an upper surface of the container 1500, but is not connected thereto. When the container 1500 is raised, a repulsive force of the spring 113 and the spring 115 is transmitted to the puncture rib 1411, thereby causing the needle 1410 to project therefrom. In addition, one end of the spring 112 and the spring 114 is connected to the upper surface of the puncture rib 1411, and the other end of the springs is connected to an inner surface of the housing of the puncture unit 1400. The spring 112 and the spring 114 press the puncture rib 1411 downward after the needle 1410 punctures the finger. In this manner, the needle 1410 is separated from the finger, and bleeding starts.

FIG. 14 illustrates an operation process of the blood collecting device 3, and FIGS. 15A to 15C illustrate a method of driving the blood collecting device 1300 according to the present invention.

A left index finger 4 is placed on the puncture hole portion 1404 on the puncture side 1403 of the blood collecting device 1300. Thereafter, the container 1500 is gripped with a right hand thumb and right index finger 4' of the hand having no puncture site, and the container 1500 is rotated in a screwing direction, or the container 1500 is lifted upward (FIG. 15A).

If the container 1500 is lifted upward, the puncture rib 1411 is pressed against an upper end surface of the container 1500 by the repulsive force of the springs 115 and 113, and disengages from the projection portion 1420. As illustrated in FIG. 15B, the repulsive force of the contracted springs 113 and 115 causes the puncture unit 101 to project from the puncture hole 102. Then, the needle 1410 pierces the finger 4, and bleeding starts from the puncture scar of the finger 4.

After the puncture is performed, the needle 1410 of the puncture unit 101 is supported by the projection 1420 as illustrated in FIG. 15C, and the tip of the needle 1410 is adjusted to a distance in which the finger is not touched. The blood 301 flows through the needle 1410, and is accumulated inside the container 1500. The collected blood confirmation portion 117 can confirm whether or not the blood is accumulated inside the container 1500 as much as the required amount for inspection. The confirmation method using the collected blood confirmation portion 117 is the same as that according to the second embodiment. A point different from that according to the second embodiment is that the blood collecting amount confirmation mechanism 506 is not provided. A small mirror 10211 (illustrated in FIG. 12B) is disposed in the necessary amount of memory for the container unit 110, and a mirror 10212 (illustrated in FIG. 12) is located below the container unit 102 so as to visibly confirm the blood collecting amount. Similarly to FIG. 12B, after specimens are collected as much as the required amount, the finger is detached from the blood collecting device 1300, and the container 1500 is covered with the lid. This prevents the collected blood from being mixed with bacteria in the open air.

Thereafter, the container 1500 is delivered to a centrifuge (not illustrated), and is installed in the centrifuge without any change, thereby, separating the blood into serums and blood cells. The container 1500 may contain chemicals such as coagulants and separating agents. In a case where the separating agents are contained, after the blood is separated using centrifuge, the blood is delivered to an analyzer (not illustrated). The container 1500, the through-hole 1401, and the puncture support portion 1412 may be coated with anticoagulants and coagulants depending on inspection items.

The blood collecting device 1300 is disposable. As materials of the container, those in which ingredients of the materials do not dissolve into the blood and do not break the blood cells are selected so as not to affect the blood. As the materials, it is conceivable to select polyethylene terephthalate, polyester, polyacrylonitrile, polymethyl methacrylate, polypropylene, polyethylene, polyamide, polystyrene, glass, and silicon. The needle 1410 may be formed of a material such as metal or a resin having some strength.

In the present embodiment, the puncture unit 1400 and the container 1500 are attached to one instrument. Accordingly, the blood can be collected into the container 1500 immediately after the puncture is performed. In addition, the container 1500 is disposed directly below the finger, and the puncture unit 1400 has the through-hole 1401. Therefore, a micro-volume of the blood 301 bleeding from the finger flows into the container 1500 through the needle 1410 immediately after the puncture is performed. In addition, when the blood is collected, the puncture hole portion 1404 is sealed with the finger. Accordingly, the blood is not exposed outward from the container 1500, no blood is lost, and the blood is not scattered to the surroundings.

That is, the blood is not scattered open air other than the container for collecting the blood, and blood can be collected in a short time after the puncture is performed.

REFERENCE SIGNS LIST

1 BLOOD COLLECTING DEVICE
2 FIXING UNIT
3 CONNECTING BODY
4 FINGER
110 MOVABLE CONTAINER UNIT
111 PROJECTION
112 CONTAINER
113 LID
120 MOVABLE PUNCTURE UNIT
121 PROJECTION
122 NEEDLE TIP
123 NEEDLE PORTION CONNECTOR
124 NEEDLE HOLDER
125 SHAFT
130 DRIVE FIXING UNIT
131 SPRING ACCOMMODATING PORTION
132 PRESSURE SOURCE
133 PUNCTURE PORTION FIXING UNIT
134 POSITIONING PORTION
140 DRIVE UNIT
141 SPHYGMOMANOMETER
142 PRESSURIZING DEVICE
201 FINGER UPPER SURFACE FIXING MEMBER
202 FINGER LOWER SURFACE FIXING MEMBER
203 COMPRESSION BODY
205 FINGER FIXING HOLDER
206 LOWER SURFACE HOLDER
207 PRESSURE SENSOR
800 BLOOD COLLECTING DEVICE
501 DISK
503 NEGATIVE PRESSURE DEVICE
504 UPPER DISK
505 LOWER DISK
506 BLOOD COLLECTING AMOUNT CONFIRMATION MECHANISM
508 NEGATIVE PRESSURE FLOW PATH
5055, 5056 LEVER
1300 BLOOD COLLECTING DEVICE
1400 PUNCTURE UNIT

1401 THROUGH-HOLE
1402 SMALL WINDOW
1410 NEEDLE
1411 PUNCTURE RIB
1500 CONTAINER

The invention claimed is:

1. A blood collecting device comprising:
a container unit that has an opening portion and a closing portion, and that holds the opening portion in a state where the opening portion faces upward;
a fixing unit that fixes a blood collecting target in a state where the blood collecting target faces the opening portion;
a pressure changing unit that pressurizes the blood collecting target or applies negative pressure into a space surrounded by the blood collecting target and the container, or that performs both of these in combination with each other;
a puncture unit that is positioned below the container unit, and that punctures the blood collecting target after pressure is changed by the pressure changing unit; and
a lid that closes the opening portion of the container containing blood,
wherein the container unit has a slide mechanism which slides with respect to the fixing unit in a horizontal direction.

2. The blood collecting device according to claim 1,
wherein the pressure changing unit includes a sphygmomanometer which serves as a compression body for pressurizing the blood collecting target by using pneumatic pressure, and which measures blood pressure while pressurizing the blood collecting target by using the compression body.

3. The blood collecting device according to claim 2, further comprising:
a pressurizing source that pressurizes the blood collecting target so that the blood pressure obtained by the sphygmomanometer is in a range of the lowest blood pressure to the highest blood pressure.

4. The blood collecting device according to claim 1, further comprising:
a cover that protects the blood collecting target after blood collecting.

5. The blood collecting device according to claim 1,
wherein all of the container unit, the fixing unit, and the puncture unit are configured to be separable from each other.

6. The blood collecting device according to claim 1, further comprising:
a blood collecting amount confirmation mechanism which confirms an amount of the blood contained inside the container unit.

7. The blood collecting device according to claim 1,
wherein at least a portion of the container unit has a transparent window.

8. A blood collecting device comprising:
an upper disk that has at least one through-hole;
a lower disk that is positioned below the upper disk, and that is rotatable independent of the upper disk;
a negative pressure source that applies negative pressure to a surrounding environment of a blood collecting target pressed against the through-hole;
a puncture unit that is fixed to the lower disk, and that punctures the blood collecting target after pressure is changed by a pressure changing unit; and
a container unit that has an opening portion and a closing portion, and that is fixed to the lower disk in a state where the opening portion faces upward.

9. The blood collecting device according to claim 8,
wherein the container unit and the puncture unit are detachably fixed to the lower disk.

10. The blood collecting device according to claim 8,
wherein at least a portion of the container unit has a transparent window.

* * * * *